United States Patent [19]
Koga et al.

[11] Patent Number: 6,143,763
[45] Date of Patent: *Nov. 7, 2000

[54] CARBOSTYRIL DERIVATIVES

[75] Inventors: Yasuo Koga, Itano-gun; Yoshito Kihara, Naruto; Minoru Okada; Takao Nishi, both of Tokushima; Yoshihiro Inoue, Kashihara; Yukio Kimura, Tokushima; Hiroyoshi Hidaka, Nagoya; Norio Fukuda, Tokushima, all of Japan

[73] Assignee: D. Western Therapeutics Institiute, Aich-ken, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/849,664

[22] PCT Filed: Oct. 4, 1996

[86] PCT No.: PCT/JP96/02892

§ 371 Date: May 29, 1998

§ 102(e) Date: May 29, 1998

[87] PCT Pub. No.: WO97/12869

PCT Pub. Date: Apr. 10, 1997

[30] Foreign Application Priority Data

Oct. 5, 1995 [JP] Japan ..................... 7-258705

[51] Int. Cl.⁷ .................. A61K 31/4704; C07D 215/227
[52] U.S. Cl. .......................... 514/312; 546/157; 546/158
[58] Field of Search .................... 546/157, 158; 514/312

[56] References Cited

U.S. PATENT DOCUMENTS 5,506,239  4/1996  Sato et al. ................ 514/312

OTHER PUBLICATIONS

Koga et al., "2(1H)–Quinolinone derivatives as novel anti–arteriostenotic agents showing anti–thrombotic and anti–hyperplastic activites," Bioorganic & Medicinal Chem. Letters, vol. 8, No. 12, pp. 1471–1476, Jun. 16, 1998.

Primary Examiner—Richard L. Raymond
Attorney, Agent, or Firm—Sughrue, Mion, Zinn Macpeak & Seas, PLLC

[57] ABSTRACT

A carbostyril derivative of the formula (1):

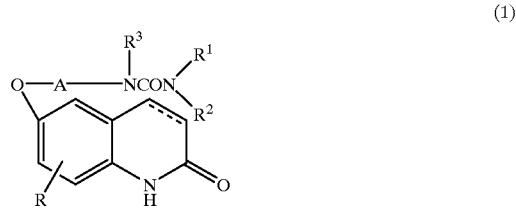

(1)

wherein A is lower alkylene, R is H, halogen or lower alkoxy, $R^1$ and $R^2$ are each lower alkyl being optionally substituted by OH, lower alkoxy, phenyl-lower alkoxy or lower alkanoyloxy; cycloalkyl being optionally substituted by OH, hydroxy-lower alkoxy or lower alkanoyloxy; or amino being optionally substituted by lower alkyl or cycloalkyl, $R^3$ is H, lower alkyl, lower alkenyl or hydroxy-lower alkyl, and the bond between 3- and 4-positions of the carbostyril nucleus is single or double, provided that when R and $R^3$ are H, $R^1$ and $R^2$ should not be either unsubstituted lower alkyl or unsubstituted cycloalkyl, or a salt thereof, which shows antithrombotic activities, intima thickening inhibitory activity, the platelet mass dissociating activity and increasing activity of the blood flow in the brain and the peripheral vessel, and hence, is useful as medicines in the prophylaxis or treatment of various ischemic diseases.

41 Claims, No Drawings

CARBOSTYRIL DERIVATIVES

This application is a 371 of PCT/JP96/02892, filed Oct. 4, 1996.

TECHNICAL FIELD

The invention relates to novel carbostyril derivatives being useful as medicines in the prophylaxis or treatment of various ischemic diseases.

BACKGROUND ART

Ischemic diseases such as thrombosis or arteriosclerosis may break out and become worse by a complicated interaction of three factors of the change in the components in the blood fluid, the abnormal blood flow and the disorder of the blood vessel wall. Although thrombosis is caused by various factors, it mainly breaks out by the disorder of the intima cells like in the case of atherosclerosis, subsequently the activation of platelets, and then by the adhesion and aggregation of platelets.

Arteriosclerosis breaks out and becomes worse by the growth of the blood vessel smooth muscle cells by the complicated interaction of the above mentioned three factors, and then by the thickening of the intima.

Thus, it is very important that a medicant being useful in the prophylaxis or treatment of ischemic diseases such as thrombosis or arteriosclerosis should essentially show both antithrombotic activity and intima thickening inhibitory activity.

There are known various carbostyril derivatives. For example, WO 93/04042 (=JP-A-5-194405) discloses carbostyril derivatives of the formula:

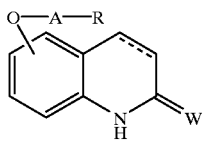

wherein A is a lower alkylene; R is —NR$^1$R$^2$, —SO$_2$NR$^3$R$^4$, or —Y—NR$^5$R$^6$; R$^1$ is —(CO)$_1$—B—(CO)$_m$—NR$^7$R$^8$ or —SO$_2$—D—R$^9$; R$^2$ is H, a cycloalkyl, a substituted or unsubstituted phenyl, etc.; or R$^1$ and R$^2$ may combine with the adjacent nitrogen to form a substituted or unsubstituted pyrrolidinyl; R$^3$ is H, lower alkyl, —E—(CO)$_n$—NR$^{10}$R$^{11}$, etc.; R$^4$ is H, a cycloalkyl, a substituted or unsubstituted phenyl, a heterocyclic group-substituted alkyl, etc.; Y is —NHCO—, —NHC(=S)— or —C(=S)—; R$^5$ and R$^6$ are each H, a lower alkyl, a cycloalkyl, a piperidinyl-alkyl, etc.; and W is O or S, which have a platelet aggregation inhibitory activity and a platelet adhesion inhibitory activity. Some compounds inclusive in the general formula of the present invention may fall within the scope of the general formula of this prior art, and those possibly overlapping compounds are excluded from the present invention by the proviso phrase.

U.S. Pat. Nos. 4,070,470, 4,216,220 and 4,313,947 disclose carbostyril derivatives of the formula:

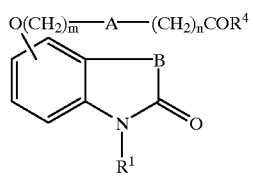

wherein R$^1$ is H, lower alkyl, lower alkenyl or aralkyl, R$^4$ is OH, alkoxy, substituted or unsubstituted amino, heterocyclic amino, etc., A is lower alkylene or vinylene, B is —CH$_2$—, —CH$_2$CH$_2$— or —CH=CH—, and m and n are 0 or a positive integer with m+n being no more than 11, which have a platelet aggregation inhibitory activity.

U.S. Pat. No. 4,298,739 discloses carbostyril derivatives of the formula:

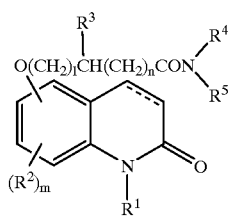

wherein R$^1$ is H, lower alkyl, lower alkenyl or phenylalkyl, R$^2$ is H, halogen, OH or phenylalkoxy, R$^3$ is H, OH or lower alkyl, R$^4$ is cycloalkyl, substituted or unsubstituted phenyl, cycloalkylalkyl, etc., R$^5$ is H, alkyl, lower alkenyl, phenyl, cycloalkyl, etc., m is 1–3, and l and n are 0 or an integer of 1–7, which have a platelet aggregation inhibitory activity.

U.S. Pat. No. 4,435,404 discloses carbostyril derivatives of the formula:

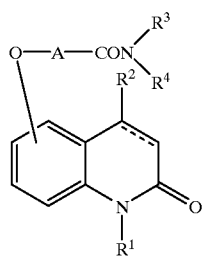

wherein R$^1$ is H, R$^2$ is H or lower alkyl, R$^3$ is hydroxy-lower alkyl having 1 to 3 hydroxy groups, lower alkanoyloxy-lower alkyl, etc., R$^4$ is cycloalkyl having 1 to 3 hydroxy groups, etc., or R$^3$ and R$^4$ form a group of the formula:

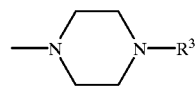

(R$^3$ is phenyl, etc.), A is lower alkylene, which have a platelet aggregation inhibitory activity.

EP-A-0450066 (published on Oct. 9, 1989) discloses carbostyril derivatives of the formula:

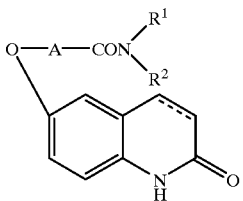

wherein $R^1$ is substituted or unsubstituted cycloalkyl-lower alkyl, cycloalkyl, substituted or unsubstituted phenyl, piperidinyl-lower alkyl, etc., $R^2$ is substituted or unsubstituted heterocyclo-lower alkyl, pyridylthio-lower alkyl, substituted or unsubstituted lower alkyl, etc., and A is an alkylene, which have a platelet aggregation inhibitory activity.

JP-A-55-79371 (published on Jun. 14, 1980) discloses carbostyril derivatives of the formula:

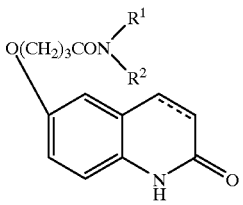

wherein $R^1$ is lower alkyl, $R^2$ is oxo-substituted cycloalkyl, which have a platelet aggregation inhibitory activity.

JP-A-57-14574 (published on Jan. 25, 1982) discloses carbostyril derivatives of the formula:

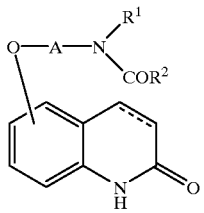

wherein $R^1$ is lower alkyl, $R^2$ is cycloalkyl or pyridyl, and A is an alkylene, which have a platelet aggregation inhibitory activity.

There are many other literatures which disclose carbostyril derivatives analogous to the compounds of the present invention.

However, those carbostyril derivatives of those known literatures as mentioned above are distinguished from the compounds of the present invention in that those known compounds other than those of the above first literature WO 93/04042 have no ureido-lower alkoxy substituent on the carbostyril nucleus.

DISCLOSURE OF THE INVENTION

The present invention relates to a novel carbostyril derivative of the following formula (1):

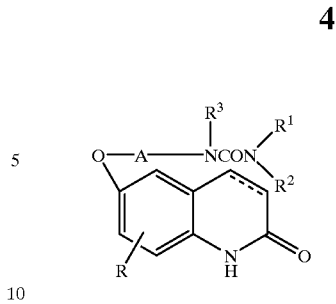

wherein A is a lower alkylene group,
R is a hydrogen atom, a halogen atom or a lower alkoxy group,
$R^1$ and $R^2$ are the same or different and are each a lower alkyl group having optionally a substituent selected from a hydroxy group, a lower alkoxy group, a phenyl-lower alkoxy group and a lower alkanoyloxy group; a cycloalkyl group having optionally a substituent selected from a hydroxy group, a hydroxy-substituted lower alkoxy group and a lower alkanoyloxy group; or an amino group having optionally a substituent selected from a lower alkyl group and a cycloalkyl group,
$R^3$ is a hydrogen atom, a lower alkyl group, a lower alkenyl group or a hydroxy-substituted lower alkyl group, and
the bond between 3- and 4-positions of the carbostyril nucleus is a single bond or a double bond,
provided that when R and $R^3$ are a hydrogen atom, $R^1$ and $R^2$ should not be either an unsubstituted lower alkyl group or an unsubstituted cycloalkyl group,
or a salt thereof.

According to the studies of the present inventors, the carbostyril derivatives (1) of the present invention and a salt thereof show both potent antithrombotic activity and intima thickening inhibitory activity in vivo, and they also show a platelet aggregation inhibitory activity, a dissociation activity of platelet mass, and an increasing activity in blood flow in the brain and the peripheral vessel, etc.

The present compounds show the pharmacological activities for a prolonged time, and show very weak effects on the circulation, e.g. very weak increasing activity in heart beat, very weak hypotensive activity, etc., and hence, they show very few side effects, especially on the heart. Besides, the present compounds are well absorbed at the digestion organs and show excellent efficiency of migration into the blood flow.

Thus, the present compounds are useful in the prophylaxis or treatment of thrombotic diseases or arteriosclerotic diseases. For example, the present compounds may clinically be used in the prophylaxis or treatment of various ischemic diseases, for example, in the prophylaxis or treatment of brain diseases such as cerebral atherosclerosis, cerebral infarction, transient cerebral ischemic attack (TIA), reversible ischemic neurological deficit (RIND), etc., heart diseases such as myocardial infarction, angina pectoris, etc., chronic arterial embolisms such as Buerger disease (thromboangiitis obliterans), embolic atherosclerosis, intermittent claudication, etc., diabetic complications such as diabetic neuropathy, diabetic dermopathy, diabetic nephropathy, etc., in the prevention of re-stenosis after interventional treatment of percutaneous transluminal coronary angioplasty (PTCA), directional coronary atherectomy (DCA), stent, etc., in the prevention of re-occlusion after the transplant of artificial organs such as artificial blood vessel or kidney, in the prevention of thrombosis or embolism during the extracorporeal circulation such as artificial kidney dialysis or operations.

Besides, the present compounds also show a potent inhibitory activity against cGMP inhibited cAMP PDE (PDE 3) which is classified by phosphodiesterase nomenclature disclosed in Molecular Pharmacology, 46, pp. 399–405 (1994).

The cyclic adenosine monophosphate (cAMP) is a representative intracellular second messenger in the living body, and decomposed and inactivated by phosphodiesterase (hereinafter, abbreviated as "PDE"). Currently, at least 7 different PDE isozyme gene families are recognized and these PDEs are widely distributed in many cell types and tissues. Thus, a PDE inhibitor increases the concentration of cAMP in tissue cells, and hence, is useful in the prophylaxis or treatment of various diseases caused by the decrease in cAMP level which is induced by the abnormal metabolism of cAMP.

As is disclosed in Pharmacology & Therapeutics, 51, pp. 13–33 (1991), Trends in Pharmacological Science, 11, pp. 150–155 (1990), Trends in Pharmacological Science, 12, pp. 19–27 (1991), the present compounds having a PDE inhibitory activity can also be clinically used in the prophylaxis or treatment of obesity based on the lipocatabolic action in fatty cells, or in the treatment of allergic diseases and asthma based on the inhibitory activity of the release of the chemical mediator from inflammatory cells in addition to the clinical use based on the above mentioned antithrombotic activity and the intima thickening inhibitory activity.

Each group in the above formula (1) specifically includes the following groups.

The "lower alkylene group" includes a straight chain or branched chain alkylene group having 1 to 6 carbon atoms, for example, methylene, ethylene, methylmethylene, trimethylene, 2-methyltrimethylene, 2,2-dimethyltrimethylene, tetramethylene, pentamethylene, hexamethylene, 2-ethyltrimethylene, 1-methyltrimethylene, and the like.

The "lower alkanoyloxy group" includes a straight chain or branched chain alkanoyloxy group having 2 to 6 carbon atoms, for example, acetyloxy, propionyloxy, butyryloxy, isobutyryloxy, pentanoyloxy, t-butylcarbonyloxy, hexanoyloxy, and the like.

The "lower alkyl group having optionally a substituent selected from a hydroxy group, a lower alkoxy group, a phenyl-lower alkoxy group and a lower alkanoyloxy group" includes a straight chain or branched chain alkyl group having 1 to 6 carbon atoms which may optionally have 1 to 3 substituents selected from a hydroxy group, a straight chain or branched chain alkoxy group having 1 to 6 carbon atoms, a phenylalkoxy group wherein the alkoxy moiety is a straight chain or branched chain alkoxy group having 1 to 6 carbon atoms, and a straight chain or branched chain alkanoyloxy group having 2 to 6 carbon atoms, for example, methyl, ethyl, propyl, isopropyl, butyl, t-butyl, pentyl, hexyl, 2-hydroxyethyl, 3-hydroxypropyl, 4-hydroxybutyl, 2-hydroxybutyl, 3-hydroxybutyl, 5-hydroxypentyl, 2-hydroxypentyl, 3-hydroxypentyl, 4-hydroxypentyl, 6-hydroxyhexyl, 2-hydroxyhexyl, 3-hydroxyhexyl, 4-hydroxyhexyl, 1-methyl-2-hydroxyethyl, 2-hydroxypropyl, 1,1-dimethyl-2-hydroxyethyl, 1,2-dihydroxyethyl, 2,2-dihydroxyethyl, 1,3-dihydroxypropyl, 2,3-dihydroxypropyl, 1,2,3-trihydroxypropyl, 1,4-dihydroxybutyl, 2,4-dihydroxybutyl, 3,4-dihydroxybutyl, 1,2-dihydroxybutyl, 2,3-dihydroxybutyl, 1,3-dihydroxybutyl, 2,2-dihydroxybutyl, 1,2,3-trihydroxybutyl, 2,3,4-trihydroxybutyl, 2,3-dihydroxypentyl, 3,4-dihydroxypentyl, 3,5-dihydroxypentyl, 2,3,4-trihydroxypentyl, 3,4,5-trihydroxypentyl, 2,4,5-trihydroxypentyl, 2,3-dihydroxyhexyl, 2,5-dihydroxyhexyl, 2,6-dihydroxyhexyl, 3,4-dihydroxyhexyl, 4,5-dihydroxyhexyl, 4,6-dihydroxyhexyl, 5,6-dihydroxyhexyl, 2,3,4-trihydroxyhexyl, 3,4,5-trihydroxyhexyl, 4,5,6-trihydroxyhexyl, 3,4-diacetyloxy-5-hydroxyhexyl, acetyloxymethyl, 2-acetyloxyethyl, 3-acetyloxypropyl, 2-acetyloxybutyl, 5-propanoyloxypentyl, 6-butyryloxyhexyl, pentanoyloxymethyl, 4-hexanoyloxybutyl, 3,4,5-triacetyloxyhexyl, 2,3-diacetyloxypropyl, 2-ethoxypropyl, 2-benzyloxypropyl, 2-ethoxybutyl, 2-benzyloxybutyl, 2-methoxyethyl, 4-propoxybutyl, 2-butoxybutyl, 3-pentyloxybutyl, 5-hexyloxypentyl, 2-ethoxypentyl, 3-methoxypentyl, 4-ethoxypentyl, 6-methoxyhexyl, 2-ethoxyhexyl, 3-ethoxyhexyl, 4-methoxyhexyl, 1-methyl-2-ethoxyethyl, 1,1-dimethyl-2-ethoxyethyl, 2,3-diethoxypropyl, 2-(2-phenylethoxy)ethyl, 4-(1-phenylethoxy)butyl, 2-(3-phenylpropoxy)butyl, 3-(4-phenylbutoxy)butyl, $^5$-(5-phenylpentyloxy)pentyl, 2-(6-phenylhexyloxy)pentyl, 3-benzyloxypentyl, 4-benzyloxypentyl, 6-(2-phenylethoxy)hexyl, 2-(1-phenylethoxy)hexyl, 3-benzyloxyhexyl, 4-benzyloxyhexyl, 1-methyl-2-benzyloxyethyl, 1,1-dimethyl-2-(2-phenylethoxy)ethyl, 2,3-dibenzyloxypropyl, etc.

The "cycloalkyl group having optionally a substituent selected from a hydroxy group, a hydroxy-substituted lower alkoxy group and a lower alkanoyloxy group" includes a cycloalkyl group having 3 to 8 carbon atoms which may optionally have 1 to 3 substituents selected from a hydroxy group, a straight chain or branched chain alkoxy group having 1 to 6 carbon atoms and being substituted by 1 to 3 hydroxy groups, and a straight chain or branched chain alkanoyloxy group having 2 to 6 carbon atoms, for example, cyclopropyl, cyclobutyl, cyclopentyl, cyclohexyl, cycloheptyl, cyclooctyl, 2-hydroxycyclohexyl, 2-hydroxycyclopropyl, 3-hydroxycyclobutyl, 2-hydroxycyclopentyl, 4-hydroxycycloheptyl, 3-hydroxycyclooctyl, 3-hydroxycyclohexyl, 4-hydroxycyclohexyl, 2,3-dihydroxycyclohexyl, 3,4-dihydroxycyclohexyl, 2,4,6-trihydroxycyclohexyl, 2-propionyloxycyclopropyl, 2-butyryloxycyclobutyl, 3-pentanoyloxycyclopentyl, 3-acetyloxycyclohexyl, 4-acetyloxycyclohexyl, 3-hexanoyloxycycloheptyl, 5-acetyloxycyclooctyl, 2,4-diacetyloxycyclohexyl, 2,3,4-triacetyloxycyclohexyl, 2-hydroxy-4-acetyloxycyclohexyl, 2-(3-hydroxypropoxy)cyclohexyl, 2-hydroxymethoxycyclopropyl, 3-(2-hydroxyethoxy)cyclobutyl, 2-(1-hydroxyethoxy)cyclopentyl, 4-(3-hydroxypropoxy)cycloheptyl, 3-(4-hydroxybutoxy)cyclooctyl, 3-(5-hydroxypentyloxy)cyclohexyl, 4-(2-hydroxyethoxy)cyclohexyl, 2,3-dihydroxymethoxycyclohexyl, 2,3,4-trihydroxymethoxycyclohexyl, etc.

The "lower alkyl group" includes a straight chain or branched chain alkyl group having 1 to 6 carbon atoms, for example, methyl, ethyl, propyl, isopropyl, butyl, t-butyl, pentyl, hexyl, etc.

The "lower alkenyl group" includes a straight chain or branched chain alkenyl group having 2 to 6 carbon atoms, for example, vinyl, allyl, 2-butenyl, 3-butenyl, 1-methylallyl, 2-pentenyl, 2-hexenyl, etc.

The "lower alkoxy group" includes a straight chain or branched chain alkoxy group having 1 to 6 carbon atoms, for example, methoxy, ethoxy, propoxy, isopropoxy, butoxy, t-butoxy, pentyloxy, hexyloxy, etc.

The "phenyl-lower alkoxy group" includes a phenyl-alkoxy group wherein the alkoxy moiety is a straight chain or branched chain alkoxy group having 1 to 6 carbon atoms, for example, benzyloxy, 1-phenylethoxy, 2-phenylethoxy, 3-phenylpropoxy, 4-phenylbutoxy, 5-phenylpentyloxy, 6-phenylhexyloxy, 1,1-dimethyl-2-phenylethoxy, 2-methyl-3-phenylpropoxy, etc.

The "hydroxy-substituted lower alkyl group" includes a straight chain or branched chain alkyl group having 1 to 6 carbon atoms and being substituted by 1 to 3 hydroxy groups, for example, hydroxymethyl, 2-hydroxyethyl, 3-hydroxypropyl, 4-hydroxybutyl, 2-hydroxybutyl, 3-hydroxybutyl, 5-hydroxypentyl, 2-hydroxypentyl, 3-hydroxypentyl, 4-hydroxypentyl, 6-hydroxyhexyl, 2-hydroxyhexyl, 3-hydroxyhexyl, 4-hydroxyhexyl, 1-methyl-2-hydroxyethyl, 2-hydroxypropyl, 1,1-dimethyl-2-hydroxyethyl, 1,2-dihydroxyethyl, 2,2-dihydroxyethyl, 1,3-dihydroxypropyl, 2,3-dihydroxypropyl, 1,2,3-trihydroxypropyl, 1,4-dihydroxybutyl, 2,4-dihydroxybutyl, 3,4-dihydroxybutyl, 1,2-dihydroxybutyl, 2,3-dihydroxybutyl, 1,3-dihydroxybutyl, 2,2-dihydroxybutyl, 1,2,3-trihydroxybutyl, 2,3,4-trihydroxybutyl, 2,3-dihydroxypentyl, 3,4-dihydroxypentyl, 3,5-dihydroxypentyl, 2,3,4-trihydroxypentyl, 3,4,5-trihydroxypentyl, 2,4,5-trihydroxypentyl, 2,3-dihydroxyhexyl, 2,5-dihydroxyhexyl, 2,6-dihydroxyhexyl, 3,4-dihydroxyhexyl, 4,5-dihydroxyhexyl, 4,6-dihydroxyhexyl, 5,6-dihydroxyhexyl, 2,3,4-trihydroxyhexyl, 3,4,5-trihydroxyhexyl, 4,5,6-trihydroxyhexyl, etc.

The "halogen atom" is fluorine atom, chlorine atom, bromine atom, and iodine atom.

The "amino group having optionally a substituent selected from a lower alkyl group and a cycloalkyl group" includes an amino group having optionally 1 to 2 substituents selected from a straight chain or branched chain alkyl group having 1 to 6 carbon atoms and a cycloalkyl group having 3 to 8 carbon atoms, for example, amino, methylamino, ethylamino, propylamino, isopropylamino, butylamino, t-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, cyclopropyl amino, cyclobutyl amino, cyclopentyl amino, cyclohexylamino, cycloheptylamino, cyclooctylamino, N-cyclopropyl-N-cyclohexylamino, N-methyl-N-cyclohexylamino, N-methyl-N-cyclooctylamino, etc.

The "hydroxy-substituted lower alkoxy group" includes a straight chain or branched chain alkoxy group having 1 to 6 carbon atoms and being substituted by 1 to 3 hydroxy groups, for example, hydroxymethoxy, 2-hydroxyethoxy, 3-hydroxypropoxy, 4-hydroxybutoxy, 2-hydroxybutoxy, 3-hydroxybutoxy, 5-hydroxypentyloxy, 2-hydroxypentyloxy, 3-hydroxypentyloxy, 4-hydroxypentyloxy, 6-hydroxyhexyloxy, 2-hydroxyhexyloxy, 3-hydroxyhexyloxy, 4-hydroxyhexyloxy, 1-methyl-2-hydroxyethoxy, 2-hydroxypropoxy, 1,1-dimethyl-2-hydroxyethoxy, 1,2-dihydroxyethoxy, 2,2-dihydroxyethoxy, 1,3-dihydroxypropoxy, 2,3-dihydroxyproopoxy, 1,2,3-trihydroxypropoxy, 1,4-dihydroxybutoxy, 2,4-dihydroxybutoxy, 3,4-dihydroxybutoxy, 1,2-dihydroxybutoxy, 2,3-dihydroxybutoxy, 1,3-dihydroxybutoxy, 2,2-dihydroxybutoxy, 1,2,3-trihydroxybutoxy, 2,3,4-trihydroxybutoxy, 2,3-dihydroxypentyloxy, 3,4-dihydroxypentyloxy, 3,5-dihydroxypentyloxy, 2,3,4-trihydroxypentyloxy, 3,4,5-trihydroxypentyloxy, 2,4,5-trihydroxypentyloxy, 2,3-dihydroxyhexyloxy, 2,5-dihydroxyhexyloxy, 2,6-dihydroxyhexyloxy, 3,4-dihydroxyhexyloxy, 4,5-dihydroxyhexyloxy, 4,6-dihydroxyhexyloxy, 5,6-dihydroxyhexyloxy, 2,3,4-trihydroxyhexyloxy, 3,4,5-trihydroxyhexyloxy, 4,5,6-trihydroxyhexyloxy, etc.

The present invention especially includes the following compounds:

(1) The carbostyril derivative of the formula (1) wherein $R^1$ and $R^2$ are a lower alkyl group having optionally a substituent selected from a hydroxy group, a lower alkoxy group, a phenyl-lower alkoxy group and a lower alkanoyloxy group, $R^3$ is a hydrogen atom and A is a lower alkylene group, or a salt thereof.

(2) The carbostyril derivative of the formula (1) wherein $R^1$ is a lower alkyl group having optionally a substituent selected from a hydroxy group, a lower alkoxy group, a phenyl-lower alkoxy group and a lower alkanoyloxy group, $R^2$ is a cycloalkyl group having optionally a substituent selected from a hydroxy group, a hydroxy-substituted lower alkoxy group and a lower alkanoyloxy group, $R^3$ is a hydrogen atom and A is a lower alkylene group, or a salt thereof.

(3) The carbostyril derivative of the formula (1) wherein $R^1$ and $R^2$ are a lower alkyl group having optionally a substituent selected from a hydroxy group, a lower alkoxy group, a phenyl-lower alkoxy group and a lower alkanoyloxy group, $R^3$ is a lower alkyl group and A is a lower alkylene group, or a salt thereof.

(4) The carbostyril derivative of the formula (1) wherein $R^1$ is a lower alkyl group having optionally a substituent selected from a hydroxy group, a lower alkoxy group, a phenyl-lower alkoxy group and a lower alkanoyloxy group, $R^2$ is a cycloalkyl group having optionally a substituent selected from a hydroxy group, a hydroxy-substituted lower alkoxy group and a lower alkanoyloxy group, $R^3$ is a lower alkyl group and A is a lower alkylene group, or a salt thereof.

(5) The carbostyril derivative of the formula (1) wherein $R^1$ and $R^2$ are a lower alkyl group having optionally a substituent selected from a hydroxy group, a lower alkoxy group, a phenyl-lower alkoxy group and a lower alkanoyloxy group, $R^3$ is a lower alkenyl group and A is a lower alkylene group, or a salt thereof.

(6) The carbostyril derivative of the formula (1) wherein $R^1$ is a lower alkyl group having optionally a substituent selected from a hydroxy group, a lower alkoxy group, a phenyl-lower alkoxy group and a lower alkanoyloxy group, $R^2$ is a cycloalkyl group having optionally a substituent selected from a hydroxy group, a hydroxy-substituted lower alkoxy group and a lower alkanoyloxy group, $R^3$ is a lower alkenyl group and A is a lower alkylene group, or a salt thereof.

(7) The carbostyril derivative of the formula (1) wherein $R^1$ and $R^2$ are a cycloalkyl group having optionally a substituent selected from a hydroxy group, a hydroxy-substituted lower alkoxy group and a lower alkanoyloxy group, $R^3$ is a hydrogen atom and A is a lower alkylene group, or a salt thereof.

(8) The carbostyril derivative of the formula (1) wherein $R^1$ and $R^2$ are a cycloalkyl group having optionally a substituent selected from a hydroxy group, a hydroxy-substituted lower alkoxy group and a lower alkanoyloxy group, $R^3$ is a lower alkyl group and A is a lower alkylene group, or a salt thereof.

(9) The carbostyril derivative of the formula (1) wherein $R^1$ and $R^2$ are a cycloalkyl group having optionally a substituent selected from a hydroxy group, a hydroxy-substituted lower alkoxy group and a lower alkanoyloxy group, $R^3$ is a lower alkenyl group and A is a lower alkylene group, or a salt thereof.

(10) The carbostyril derivative of the formula (1) wherein $R^1$ and $R^2$ are a lower alkyl group having optionally a substituent selected from a hydroxy group, a lower alkoxy group, a phenyl-lower alkoxy group and a lower alkanoyloxy group, $R^3$ is a hydroxy-substituted lower alkyl group and A is a lower alkylene group, or a salt thereof.

(11) The carbostyril derivative of the formula (1) wherein $R^1$ is a lower alkyl group having optionally a substituent selected from a hydroxy group, a lower alkoxy group, a phenyl-lower alkoxy group and a lower alkanoyloxy group, $R^2$ is a cycloalkyl group having optionally a substituent selected from a hydroxy group, a hydroxy-substituted lower alkoxy group and a lower alkanoyloxy group, $R^3$ is a hydroxy-substituted lower alkyl group and A is a lower alkylene group, or a salt thereof.

(12) The carbostyril derivative of the formula (1) wherein $R^1$ and $R^2$ are a cycloalkyl group having optionally a substituent selected from a hydroxy group, a hydroxy-substituted lower alkoxy group and a lower alkanoyloxy group, $R^3$ is a hydroxy-substituted lower alkyl group and A is a lower alkylene group, or a salt thereof.

(13) The carbostyril derivative of the formula (1) wherein $R^1$ and $R^2$ are an amino group having optionally a substituent selected from a lower alkyl group and a cycloalkyl group, $R^3$ is a hydrogen atom and A is a lower alkylene group, or a salt thereof.

(14) The carbostyril derivative of the formula (1) wherein $R^1$ is in amino group having optionally a substituent selected from a lower alkyl group and a cycloalkyl group, $R^2$ is a lower alkyl group having optionally a substituent selected from a hydroxy group, a lower alkoxy group, a phenyl-lower alkoxy group and a lower alkanoyloxy group, $R^3$ is a hydrogen atom and A is a lower alkylene group, or a salt thereof.

(15) The carbostyril derivative of the formula (1) wherein $R^1$ is an amino group having optionally a substituent selected from a lower alkyl group and a cycloalkyl group, $R^2$ is a cycloalkyl group having optionally a substituent selected from a hydroxy group, a hydroxy-substituted lower alkoxy group and a lower alkanoyloxy group, $R^3$ is a hydrogen atom and A is a lower alkylene group, or a salt thereof.

(16) The carbostyril derivative of the formula (1) wherein $R^1$ and $R^2$ are an amino group having optionally a substituent selected from a lower alkyl group and a cycloalkyl group, $R^3$ is a lower alkyl group and A is a lower alkylene group, or a salt thereof.

(17) The carbostyril derivative of the formula (1) wherein $R^1$ is an amino group having optionally a substituent selected from a lower alkyl group and a cycloalkyl group, $R^2$ is a lower alkyl group having optionally a substituent selected from a hydroxy group, a lower alkoxy group, a phenyl-lower alkoxy group and a lower alkanoyloxy group, $R^3$ is a lower alkyl group and A is a lower alkylene group, or a salt thereof.

(18) The carbostyril derivative of the formula (1) wherein $R^1$ is an amino group having optionally a substituent selected from a lower alkyl group and a cycloalkyl group, $R^2$ is a cycloalkyl group having optionally a substituent selected from a hydroxy group, a hydroxy-substituted lower alkoxy group and a lower alkanoyloxy group, $R^3$ is a lower alkyl group and A is a lower alkylene group, or a salt thereof.

(19) The carbostyril derivative of the formula (1) wherein $R^1$ and $R^2$ are an amino group having optionally a substituent selected from a lower alkyl group and a cycloalkyl group, $R^3$ is a lower alkenyl group and A is a lower alkylene group, or a salt thereof.

(20) The carbostyril derivative of the formula (1) wherein $R^1$ is an amino group having optionally a substituent selected from a lower alkyl group and a cycloalkyl group, $R^2$ is a lower alkyl group having optionally a substituent selected from a hydroxy group, a lower alkoxy group, a phenyl-lower alkoxy group and a lower alkanoyloxy group, $R^3$ is a lower alkenyl group and A is a lower alkylene group, or a salt thereof.

(21) The carbostyril derivative of the formula (1) wherein $R^1$ is an amino group having optionally a substituent selected from a lower alkyl group and a cycloalkyl group, $R^2$ is a cycloalkyl group having optionally a substituent selected from a hydroxy group, a hydroxy-substituted lower alkoxy group and a lower alkanoyloxy group, $R^3$ is a lower alkenyl group and A is a lower alkylene group, or a salt thereof.

(22) The carbostyril derivative of the formula (1) wherein $R^1$ and $R^2$ are an amino group having optionally a substituent selected from a lower alkyl group and a cycloalkyl group, $R^3$ is a hydroxy-substituted lower alkyl group and A is a lower alkylene group, or a salt thereof.

(23) The carbostyril derivative of the formula (1) wherein $R^1$ is an amino group having optionally a substituent selected from a lower alkyl group and a cycloalkyl group, $R^2$ is a lower alkyl group having optionally a substituent selected from a hydroxy group, a lower alkoxy group, a phenyl-lower alkoxy group and a lower alkanoyloxy group, $R^3$ is a hydroxy-substituted lower alkyl group and A is a lower alkylene group, or a salt thereof.

(24) The carbostyril derivative of the formula (1) wherein $R^1$ is an amino group having optionally a substituent selected from a lower alkyl group and a cycloalkyl group, $R^2$ is a cycloalkyl group having optionally a substituent selected from a hydroxy group, a hydroxy-substituted lower alkoxy group and a lower alkanoyloxy group, $R^3$ is a hydroxy-substituted lower alkyl group and A is a lower alkylene group, or a salt thereof.

(25) 6-{3-[3-(trans-2-Hydroxycyclohexyl)-3-cyclopropylureido]propoxy}-carbostyril

(26) (S,S)-(+)-6-{3-[3-(2-Hydroxycyclohexyl)-3-cyclopropylureido]propoxy}-carbostyril

(27) (R,R)-(−)-6-{3-[3-(2-Hydroxycyclohexyl)-3-cyclopropylureido]propoxy}-carbostyril

(28) 6-{3-[3-(2-Hydroxycyclobutyl)-3-cyclopropylureido]propoxy}-carbostyril

The carbostyril derivatives of the above formula (1) can be prepared by various processes, for example, by the following processes.

Reaction Scheme-1 wherein R, $R^1$, $R^2$, $R^3$, A and the bond between 3- and 4-positions of the carbostyril nucleus are the same as defined above, X is a halogen atom, a lower alkanesulfonyloxy group, an arylsulfonyloxy group, or an aralkylsulfonyloxy group.

The reaction of the compound (2) and the compound (3) is carried out in a suitable solvent, preferably by using a basic compound as a de-halogen hydride agent at a temperature from room temperature to 200° C., preferably at a temperature from room temperature to 150° C., for about 1 hour to about 75 20 hours. The suitable solvent includes, for example, lower alcohols (e.g. methanol, ethanol, isopropanol, etc.), ketones (e.g. acetone, methyl ethyl ketone, etc.), ethers (e.g. diethyl ether, dioxane, diethylene glycol dimethyl ether, etc.), aromatic hydrocarbons (e.g. benzene, toluene, xylene, etc.), dimethylformamide, dimethyl sulfoxide, hexamethylphosphoric triamide, etc. The basic compound used as a de-halogen hydride agent includes, for example, inorganic bases (e.g. sodium hydroxide, potassium hydroxide, sodium carbonate, potassium carbonate, sodium methoxide, sodium ethoxide, potassium ethoxide, sodium hydride, metal potassium, sodium amide, etc.), or organic bases (e.g. pyridine, quinoline, triethylamine, tripropylamine, etc.). There may be added an alkali metal iodide such as potassium iodide, sodium iodide, as a reaction promoter. The amount of the compound (3) is not critical, but it is usually in the range of 1 mole to 5 moles, preferably in the range of 1 mole to 3 moles, to 1 mole of the compound (2).

In the above Reaction Scheme-1, the halogen atom for X is fluorine atom, chlorine atom, bromine atom or iodine atom. The lower alkanesulfonyloxy group for X includes methanesulfonyloxy, ethanesulfonyloxy, isopropanesulfonyloxy, propanesulfonyloxy, butanesulfonyloxy, t-butanesulfonyloxy, pentanesulfonyloxy, hexanesulfonyloxy, etc. The arylsulfonyloxy group for X includes a substituted or unsubstituted arylsulfonyloxy group such as phenylsulfonyloxy, 4-methylphenylsulfonyloxy, 2-methylphenylsulfonyloxy, 4-nitro- phenylsulfonyloxy, 4-methoxyphenylsulfonyloxy, 3-chlorophenylsulfonyloxy, α-naphthylphenylsulfonyloxy, etc. The aralkylsulfonyloxy group for X includes a substituted or unsubstituted aralkylsulfonyloxy group such as benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy, α-naphthylmethylsulfonyloxy, etc.

Reaction Scheme-2

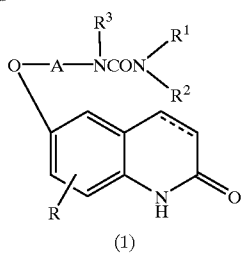

wherein R, $R^1$, $R^2$, $R^3$, A, X and the bond between 3- and 4-positions of the carbostyril nucleus are the same as defined above, and $X^1$ is a halogen atom.

The reaction of the compound (4) and the compound (5) is carried out in a suitable solvent or without a solvent in the presence or absence of a basic compound. The reaction is usually carried out at a temperature from room temperature to 200° C., preferably at a temperature from room temperature to 150° C., for 1 hour to about 30 hours. The solvent includes, for example, ethers (e.g. dioxane, tetrahydrofuran, ethylene glycol dimethyl ether, diethyl ether, etc.), aromatic hydrocarbons (e.g. benzene, toluene, xylene, etc.), halogenated hydrocarbons (e.g. dichloromethane, chloroform, carbon tetrachloride, etc.), lower alcohols (e.g. methanol, ethanol, isopropanol, etc.), water, polar solvents (e.g. dimethylformamide, dimethyl sulfoxide, hexamethylphosphoric triamide, pyridine, acetone, acetonitrile, etc.), or a mixture thereof. The basic compound includes, for example, inorganic bases (e.g. potassium carbonate, sodium carbonate, sodium hydroxide, potassium hydroxide, sodium hydrogen carbonate, potassium hydrogen carbonate, sodium amide, sodium hydride, potassium hydride, etc.), organic bases (e.g. triethylamine, tripropylamine, pyridine, quinoline, etc.), etc. There may be added an alkali metal iodide (e.g. potassium iodide, sodium iodide, etc.) as a reaction promoter. The compound (5) may usually be used at least in an equimolar amount, preferably in an excess amount, to 1 mole of the compound (4). When the compound (5) is vaporous, the reaction may be carried out in a sealed tube.

In the above Reaction Scheme-2, the halogen atom for $X^1$ is fluorine atom, chlorine atom, bromine atom or iodine atom.

The reaction of the compound (6) and the compound (7) is carried out under the same conditions as those in the reaction of the compound (2) and the compound (3) in the above Reaction Scheme-1.

Reaction Scheme-3

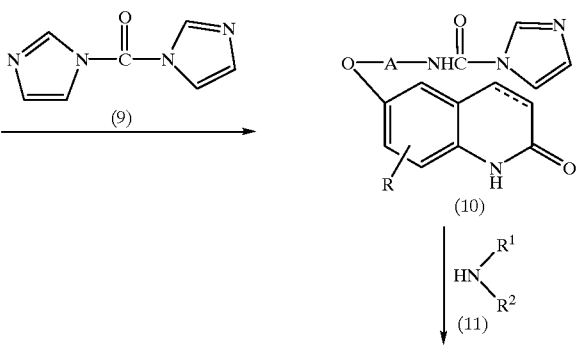

-continued

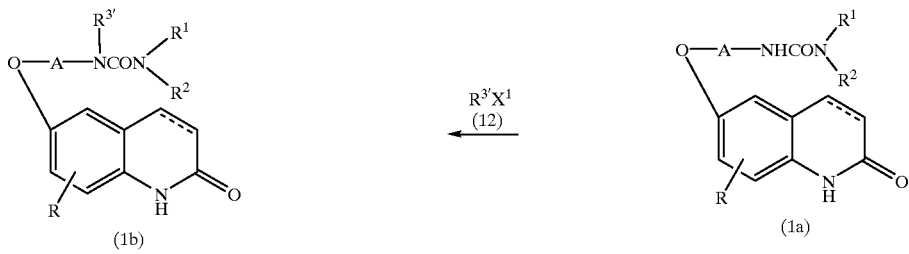

wherein R, $R^1$, $R^2$, A, $X^1$ and the bond between 3- and 4-positions of the carbostyril nucleus are the same as defined above, and $R^{3'}$ is a lower alkyl group, a lower alkenyl group or a hydroxy-substituted lower alkyl group.

The reaction of the compound (8) and the compound (9) is carried out in the presence of imidazole in a suitable solvent. The solvent may be the same solvents for the reaction of the compound (4) and the compound (5) in the above Reaction Scheme-2. The compound (9) is usually used at least in an equimolar amount, preferably in an amount of 1 mole to 1.5 mole, to 1 mole of the compound (8). Imidazole is usually used at least in an equimolar amount, preferably in an amount of 1 mole to 4 moles, to 1 mole of the compound (8). The reaction is usually carried out at a temperature from −20° C. to 150° C., preferably at a temperature from −20° C. to about 100° C., for 1 hour to about 30 hours.

The reaction of the compound (10) and the compound (11) is carried out in a suitable solvent. The solvent may be the same solvents for the reaction of the compound (4) and the compound (5) in the above Reaction Scheme-2. The compound (11) is usually used at least in an equimolar amount, preferably in an amount of 1 mole to 1.5 mole, to 1 mole of the compound (10). The reaction is usually carried out at a temperature from room temperature to 150° C., preferably at a temperature from room temperature to about 100° C., for 1 hour to about 15 hours.

The reaction of the compound (1a) and the compound (12) is carried out under the same condition as those in the reaction of the compound (2) and the compound (3) in the above Reaction Scheme-i except that the compound (12) is used at least in an equimolar, preferably in an amount of 1 mole to 5 moles, to 1 mole of the compound (1a).

Reaction Scheme-4

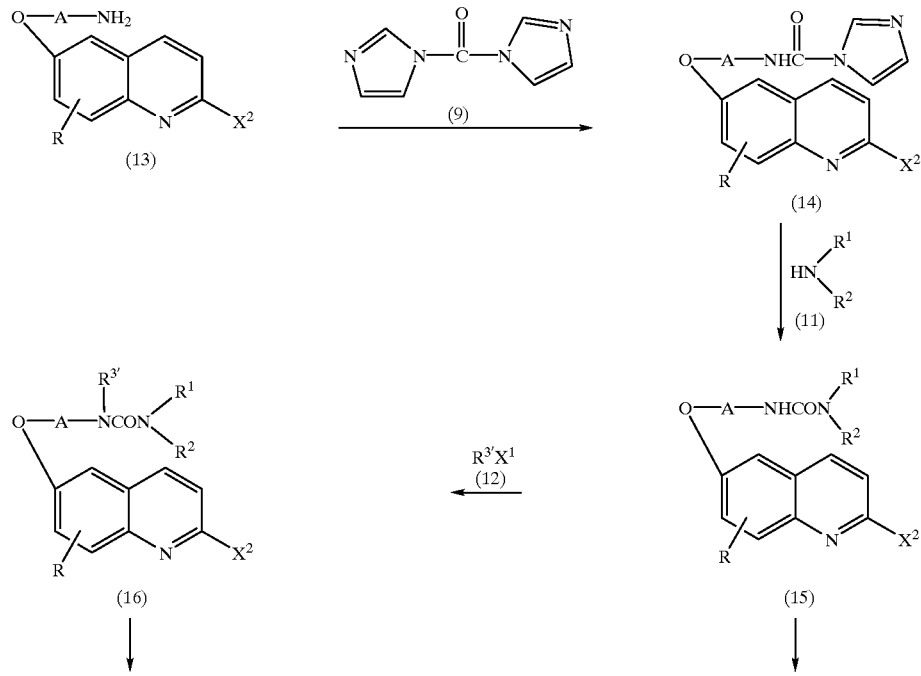

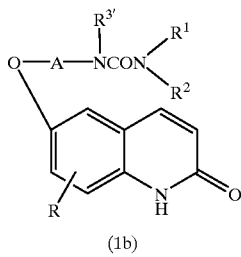

(1b)

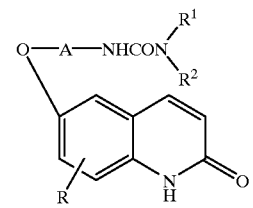

(1a)

wherein R, $R^1$, $R^2$, $R^{3'}$, A and X are the same as defined above, and $X^2$ is a halogen atom.

The reaction of the compound (13) and the compound (9) is carried out under the same conditions as those in the reaction of the compound (8) and the compound (9) in the above Reaction Scheme-3.

The reaction of the compound (14) and the compound (11) is carried out under the same conditions as those in the reaction of the compound (10) and the compound (11) in the above Reaction Scheme-3.

The reaction of the compound (15) and the compound (12) is carried out under the same conditions as those in the reaction of the compound (1a) and the compound (12) in the above Reaction Scheme-3.

The reaction of converting the compound (16) into the compound (1b), and the reaction of converting the compound (15) into the compound (1a) are carried out by heating the compound (16) or the compound (15) in the presence of a hydrohalogenic acid such as hydrochloric acid, hydrobromic acid, etc., an inorganic acid such as sulfuric acid, phosphoric acid, etc., an alkali metal hydroxide such as sodium hydroxide, potassium hydroxide, etc., an inorganic alkali metal compound such as sodium carbonate, potassium carbonate, potassium hydrogen carbonate, etc., or an organic acid such as acetic acid, at a temperature from 50° C. to 150° C., preferably at a temperature from 70° C. to 120° C., for 0.5 hour to about 24 hours.

Reaction Scheme-5

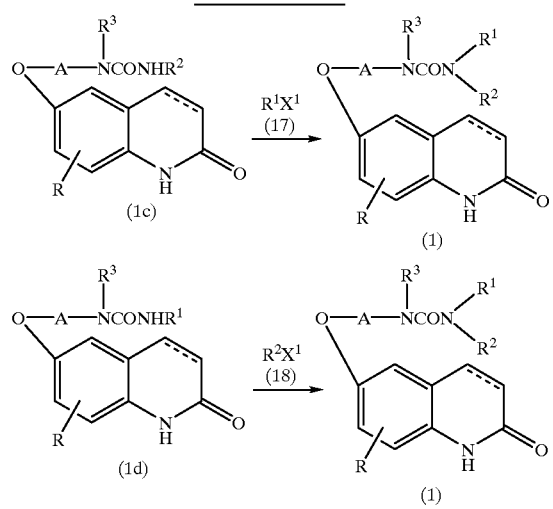

wherein R, $R^1$, $R^2$, $R^3$, A, $X^1$ and the bond between 3- and 4-positions of the carbostyril nucleus are the same as defined above.

The reaction of the compound (1c) and the compound (17), and the reaction of the compound (1d) and the compound (18) are carried out under the same conditions as those in the reaction of the compound (1a) and the compound (12) in the above Reaction Scheme-3.

Reaction Scheme-6

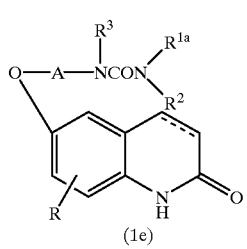

(1e)

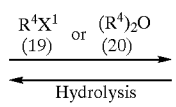

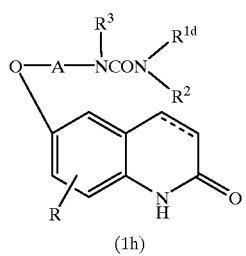

(1f)

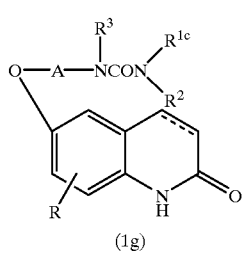

(1g)

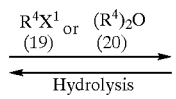

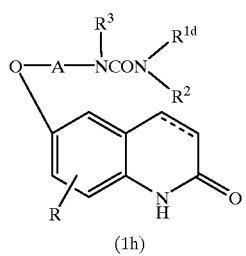

(1h)

wherein R, $R^2$, $R^3$, A, $X^1$ and the bond between 3- and 4-positions of the carbostyril nucleus are the same as defined above, $R^{1a}$ is a lower alkyl group having a hydroxy substituent, $R^{1b}$ is a lower alkyl group having a lower alkanoyloxy substituent, $R^{1c}$ is a cycloalkyl group having a hydroxy substituent, $R^{1d}$ is a cycloalkyl group having a lower alkanoyloxy substituent, and $R^4$ is a lower alkanoyl group.

The reaction of the compound (1e) and the compound (19), and the reaction of the compound (1g) and the compound (19) are carried out in a suitable inert solvent in the presence or absence of a basic compound. The inert solvent includes, for example, aromatic hydrocarbons (e.g. benzene, toluene, xylene, etc.), ethers (e.g. tetrahydrofuran, dioxane, diethylene glycol dimethyl ether, etc.), halogenated hydrocarbons (e.g. dichloromethane, chloroform, carbon tetrachloride, etc.), lower alcohols (e.g. methanol, ethanol, isopropanol, butanol, t-butanol, etc.), acetic acid, ethyl acetate, acetone, acetonitrile, pyridine, dimethyl sulfoxide, dimethylformamide, hexamethylphosphoric triamide, or a mixture thereof. The basic compound includes, for example, carbonates or hydrogen carbonates (e.g. sodium carbonate, potassium carbonate, sodium hydrogen carbonate, potassium hydrogen carbonate, etc.), alkali metal hydroxides (e.g. sodium hydroxide, potassium hydroxide, etc.), sodium hydride, sodium, potassium, sodium amide, alkali metal alkolates (e.g. sodium methylate, sodium ethylate, etc.), organic bases such as pyridine, N-ethyldiisopropylamine, dimethylaminopyridine, triethylamine, 1,5-diazabicyclo [4.3.0]nonen-5 (DBN), 1,8-biazabicyclo[5.4.0]undecen-7 (DBU), 1,4-diazabicyclo[2.2.2]octane (DABCO), etc. The ratio of the compound (1e) and the compound (19), and the ratio of the compound (1g) and the compound (19) are not critical, but the latter is usually used at least in an equimolar amount, preferably in an amount of 1 mole to 10 moles, to 1 mole of the former compound, respectively. The reaction is usually carried out at a temperature from 0° C. to about 200° C., preferably at a temperature from 0° C. to about 100° C., for 30 minutes to about 75 hours. There may be added an alkali metal halide such as sodium iodide, potassium iodide, etc., or a copper powder, as a reaction promoter.

The reaction of the compound (1e) and the compound (20), and the reaction of the compound (1g) and the compound (20) are carried out in a suitable solvent or without a solvent in the presence or absence of a basic compound, preferably in the presence of a basic compound. The solvent includes, for example, the above mentioned aromatic hydrocarbons, lower alcohols (e.g. methanol, ethanol, propanol, etc.), dimethylformamide, dimethyl sulfoxide, halogenated hydrocarbons (e.g. chloroform, methylene chloride, etc.), acetone, pyridine, etc. The basic compound includes, for example, organic bases such as triethylamine, pyridine, 4-dimethylaminopyridine, etc., sodium hydroxide, potassium hydroxide, sodium hydride, or a mixture thereof. The above reaction can be also carried out in a solvent such as acetic acid, in the presence of a mineral acid such as sulfuric acid. The compound (20) is used in an amount of 1 mole to excess amount, to 1 mole of the starting compound (1e) or (1g). The reaction is usually carried out at a temperature from 0° C. to about 200° C., preferably at a temperature from 0° C. to about 150° C., for 0.5 hour to about 20 hours.

The hydrolysis of the compound (1f) or the compound (1h) is carried out in a suitable solvent or without a solvent in the presence of an acid or a basic compound. The solvent includes, for example, water, lower alcohols (e.g. methanol, ethanol, isopropanol, etc.), ketones (e.g. acetone, methyl ethyl ketone, etc.), ethers (e.g. dioxane, tetrahydrofuran, ethylene glycol dimethyl ether, etc.), fatty acids (e.g. acetic acid, formic acid, etc.), or a mixture thereof. The acid includes, for example, mineral acids (e.g. hydrochloric acid, sulfuric acid, hydrobromic acid, etc.), organic acids (e.g. formic acid, acetic acid, aromatic sulfonic acid, etc.), etc. The basic compound includes, for example, an alkali metal carbonate (e.g. sodium carbonate, potassium carbonate, etc.), a metal hydroxide (e.g. sodium hydroxide, potassium hydroxide, calcium hydroxide, lithium hydroxide, etc.), etc. The reaction is usually carried out at a temperature from room temperature to about 200° C., preferably at a temperature from room temperature to about 150° C., for 10 minutes to about 25 hours.

The starting compounds of the formulae (3), (7), (8), (11) and (13) used in the above Reaction Schemes-1, -2,-3, and -4 are prepared by the following processes.

Reaction Scheme-7

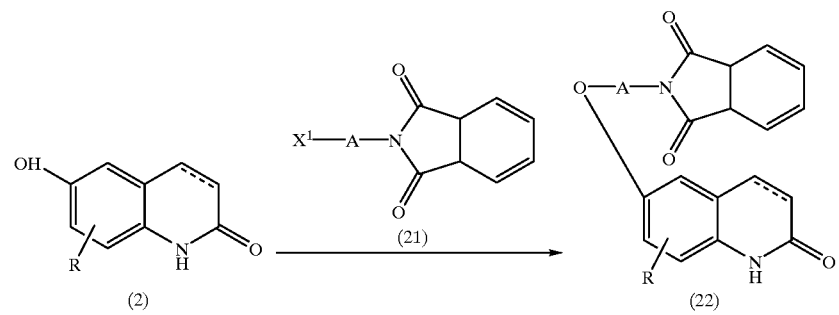

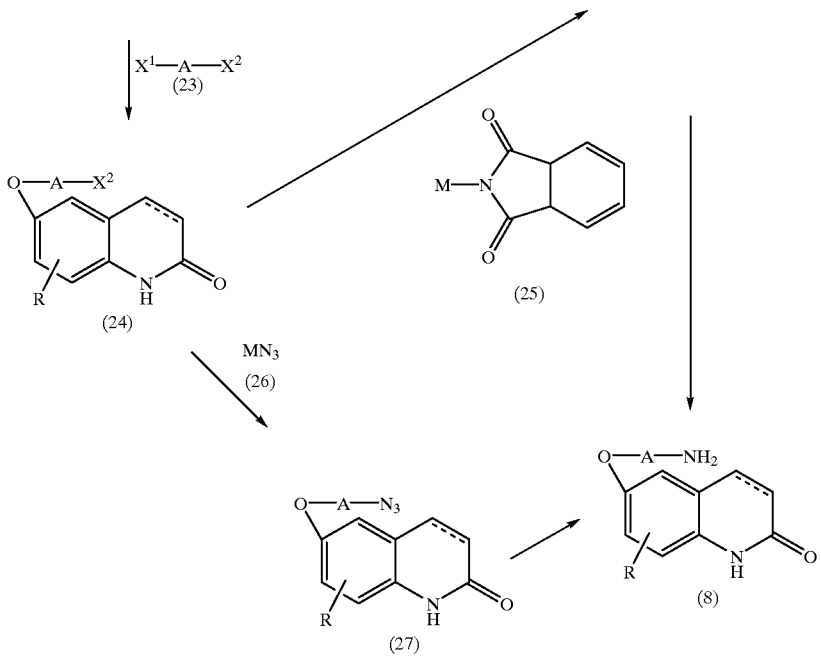

wherein R, A, $X^1$, $X^2$ and the bond between 3- and 4-positions of the carbostyril nucleus are the same as defined above, and M is an alkali metal atom such as sodium, potassium, etc.

The reaction of the compound (2) and the compound (21), an d the reaction of the compound (2) and the compound (23) are carried out under the same conditions as those in the reaction of the compound (2) and the compound (3) in the above Reaction Scheme-1.

The reaction of the compound (24) and the compound (25) is carried out in a suitable solvent at a temperature from room temperature to 200° C., preferably at a temperature from room temperature to 150° C., for 1 hour to about 15 hours. The solvent may be the same solvents for the reaction of the compound (2) and the compound (3) in the above Reaction Scheme-1. The compound (25) is usually used at least in an equimolar amount, preferably in an amount of 1 mole to 2 moles, to 1 mole of the compound (24). There may be added an alkali meta iodide such as sodium iodide, potassium iodide, or a copper powder, as a reaction promoter.

The reaction of the compound (24) and the compound (26) is carried out under the same conditions as those in the reaction of the compound (24) and the compound (25) as mentioned above.

The reaction of converting the compound (22) into the compound (8) is carried out by reacting the compound (22) with hydrazine in a suitable solvent, or by subjecting the compound (22) to hydrolysis.

The solvent used in the reaction of the compound (22) and hydrazine includes, for example, aromatic hydrocarbons (e.g. benzene, toluene, xylene, etc.), ethers (e.g. diethyl ether, dioxane, tetrahydrofuran, diethylene glycol dimethyl ether, etc.), alcohols (e.g. methanol, ethanol, isopropanol, butanol, etc.), water, acetic acid, ethyl acetate, acetone, acetonitrile, dimethyl sulfoxide, dimethylformamide, hexamethylphosphoric triamide, etc. Hydrazine is usually used at least in an equimolar amount, preferably in an amount of 1 mole to 5 moles, to 1 mole of the compound (22). The reaction is usually carried out at a temperature from room temperature to 120° C., preferably at a temperature from 0° C. to about 100° C., for 0.5 hour to 15 hours.

The hydrolysis of the compound (22) is carried out under the same conditions as those in the hydrolysis of the compound (If) in the above Reaction Scheme-6.

The reaction of converting the compound (27) into the compound (8) is carried out by subjecting the compound (27) to reduction with using a catalyst in a suitable solvent. The solvent includes, for example, water, acetic acid, alcohols (e.g. methanol, ethanol, isopropanol, etc.), hydrocarbons (e.g. hexane, cyclohexane, etc.), ethers (e.g. diethylene glycol dimethyl ether, dioxane, tetrahydrofuran, diethyl ether, etc.), esters (e.g. ethyl acetate, methyl acetate, etc.), aprotic polar solvents (e.g. N,N-dimethylformamide, etc.), or a mixture thereof. The catalyst includes, for example, palladium, palladium-black, palladium-carbon, platinum, platinum oxide, copper chromite, Raney-nickel, etc. The catalyst is used in an amount of 0.02–1 time by weight as much as the amount of the compound (27). The reaction is usually carried out at a temperature from −20° C. to about 100° C., preferably at a temperature from 0C to about 80° C., under 1 atom to 10 atms of hydrogen gas, for 0.5 hour to about 20 hours.

The reaction of converting the compound (27) into the compound (8) is also carried out by subjecting the compound (27) to reduction with using a hydrogenation reducing agent. The hydrogenation reducing agent includes, for example, lithium aluminum hydride, lithium borohydride, sodium borohydride, diborane, etc. The hydrogenation reducing agent is used at least in an equimolar amount, preferably in an amount of 1 mole to 10 moles, to 1 mole of the compound (27). The reduction reaction is usually carried out in a suitable solvent such as water, lower alcohols (e.g. methanol, ethanol, isopropanol, etc.), ethers (e.g. tetrahydrofuran, diethyl ether, diisopropyl ether, diglyme, etc.), or a mixture thereof, at a temperature from −60° C. to 150° C., preferably at a temperature from −30° C. to room temperature, for about 10 minutes to about 5 hours. In case that lithium aluminum hydride or diborane is used as a reducing agent, it is preferable to use an anhydrous solvent such as tetrahydrofuran, diethyl ether, diisopropyl ether, diglyme, etc.

Reaction Scheme-8

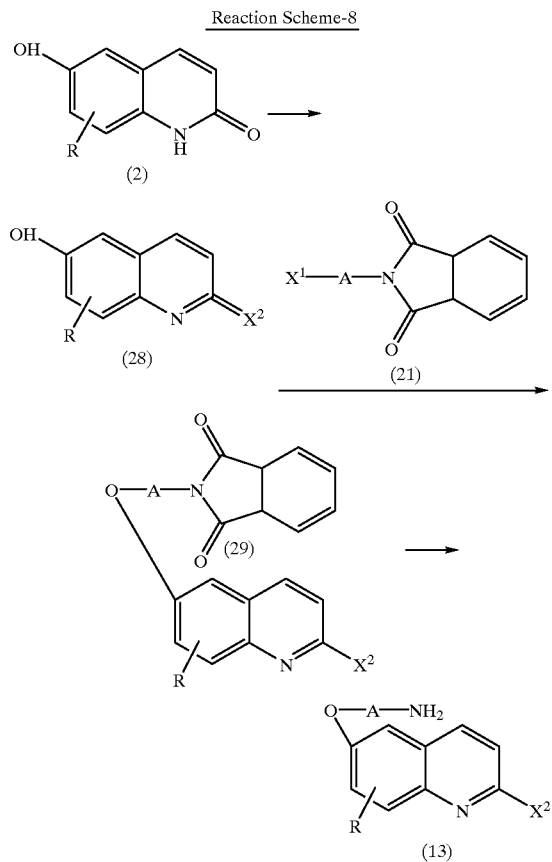

wherein R, A, X¹ and X² are the same as defined above.

The reaction of converting the compound (2) into the compound (28) is carried out by reacting the compound (2) with a halogenating agent in a suitable inert solvent or without a solvent. The halogenating agent includes, for example, N,N-diethyl-1,2,2-trichlorovinylamide, phosphorus pentachloride, phosphorus pentabromide, phosphorus oxychloride, thionyl chloride, etc. The inert solvent includes, for example, ethers (e.g. dioxane, tetrahydrofuran, etc.), halogenated hydrocarbons (e.g. dichloromethane, dichloroethane, chloroform, carbon tetrachloride, etc.), etc. The halogenating agent is usually used at least in an equimolar amount, preferably in an excess amount, to 1 mole of the compound (2). The reaction is usually carried out at a temperature from room temperature to 150° C., preferably at a temperature from room temperature to about 120° C., for about 1 hour to about 6 hours.

The reaction of the compound (28) and the compound (21) is carried out under the same conditions as those in the reaction of the compound (2) and the compound (3) in the above Reaction Scheme-1.

The reaction of converting the compound (29) into the compound (13) is carried out under the same conditions as those in the reaction of converting the compound (22) into the compound (8) in the above Reaction Scheme-7.

Reaction Scheme-9

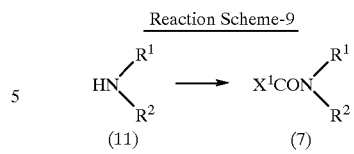

wherein $R^1$, $R^2$ and $X^1$ are the same as defined above.

The reaction of converting the compound (11) into the compound (7) is carried out by reacting the compound (11) with a carbonylating agent in the presence of a basic compound in a suitable solvent. The solvent includes, for example, halogenated hydrocarbons (e.g. dichloromethane, dichloroethane, chloroform, carbon tetrachloride, etc.), aromatic hydrocarbons (e.g. benzene, p-chlorobenzene, toluene, xylene, etc.), ethers (e.g. diethyl ether, diisopropyl ether, tetrahydrofuran, dimethoxyethane, etc.), esters (e.g. methyl acetate, ethyl acetate, etc.), alcohols (e.g. methanol, ethanol, propanol, butanol, 3-methoxy-1-butanol, ethyl cellosolve, methyl cellosolve, etc.), water, acetone, acetonitrile, pyridine, dimethyl sulfoxide, dimethylformamide, hexamethylphosphoric triamide, or a mixture thereof. The basic compound includes, for example, inorganic bases such as alkali metal carbonates or hydrogen carbonates (e.g. sodium carbonate, potassium carbonate, sodium hydrogen carbonate, potassium hydrogen carbonate, etc.), alkali metal hydroxides (e.g. sodium hydroxide, potassium hydroxide, etc.), sodium hydride, potassium hydride, etc., organic bases such as pyridine, trimethylamine, triethylamine, dimethylaniline, 1-methyl-2-pyrrolidinone (NMP), N-methylmorpholine, 1,5-diazabicyclo[4.3.0]nonen-5 (DBN), 1,8-biazabicyclo[5.4.0]undecen-7 (DBU), 1,4-diazabicyclo[2.2.2]octane (DABCO), etc. The carbonylating agent includes, for example, phosgene, diphosgene, triphosgene, etc. The carbonylating agent is usually used in an amount of 0.05 mole to 10 moles, preferably in an amount of 0.1 mole to 1 mole, to 1 mole of the compound (11). The reaction is usually carried out at a temperature from room temperature to 200° C., preferably at a temperature from room temperature to about 150° C., for 1 hour to about 10 hours.

Reaction Scheme-10

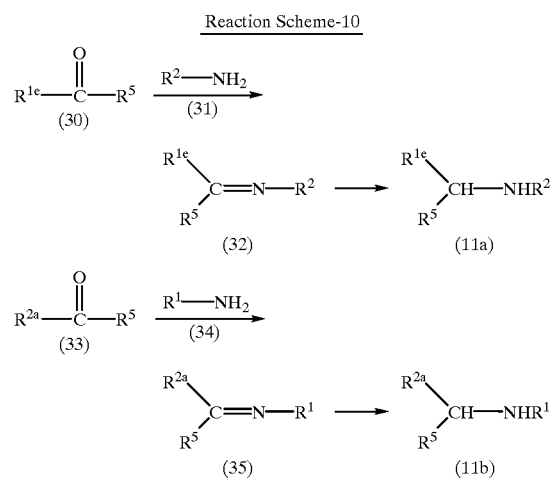

wherein $R^1$ and $R^2$ are the same as defined above, $R^{1e}$ and $R^{2a}$ are each a lower alkyl group having optionally a substituent selected from a hydroxy group, a lower alkoxy group, a phenyl-lower alkoxy group and a lower alkanoyloxy group, $R^5$ is a hydrogen atom, or $R^{1e}$ and $R^5$, or $R^{2a}$ and $R^5$ may combine together with —CO— to which they bond to form a cycloalkyl group having optionally a substituent selected from a hydroxy group, a hydroxy-substituted lower alkoxy group and a lower alkanoyloxy group.

The reaction of the compound (30) and the compound (31), and the reaction of the compound (33) and the compound (34) are carried out in the presence or absence of a dehydrating agent in a suitable solvent or without a solvent. The solvent includes, for example, alcohols (e.g. methanol, ethanol, isopropanol, etc.), aromatic hydrocarbons (e.g. benzene, toluene, xylene, etc.), aprotic polar solvents (e.g. dimethylformamide, dimethylacetamide, N-methylpyrrolidone, etc.), etc. The dehydrating agent includes, for example, a conventional drying agent used for the dehydration of a solvent such as molecular sieves, mineral acids (e.g. hydrochloric acid, sulfuric acid, boron trifluoride, etc.), organic acids (e.g. p-toluenesulfonic acid, etc.), etc. The reaction is usually carried out at a temperature from room temperature to about 200° C., preferably at a temperature from room temperature to about 150° C., for 1 hour to about 48 hours. The amount of the compound (31) or the compound (34) is not critical, but they are usually used at least in an equimolar amount, preferably in an amount of 1 mole to 15 moles, to 1 mole of the compound (30) or the compound (33), respectively. The dehydrating agent is used in an excess amount in the case of a drying agent. In the case of an acid, it is used in a catalytic amount. The compound (32) or the compound (35) thus obtained is used in the subsequent reduction reaction without isolation.

The reduction of the compound (32) or the compound (35) gives the compound (11a) or the compound (1b), respectively. The reduction reaction may be carried out by a conventional method, for example, by the reduction with using a hydrogenation reducing agent. The hydrogenation reducing agent includes, for example, lithium aluminum hydride, sodium borohydride, diborane, etc. The reducing agent is usually used at least in an equimolar amount, preferably in an amount of 1 mole to 10 moles, to 1 mole of the compound (32) or the compound (35). The reduction is usually carried out in a suitable solvent such as water, lower alcohols (e.g. methanol, ethanol, isopropanol, etc.), ethers (e.g. tetrahydrofuran, diethyl ether, diglyme, etc.), etc. at a temperature from 60° C. to about 50° C., preferably at a temperature from −30° C. to room temperature, for 10 minutes to about 5 hours. In the case that lithium aluminum hydride or diborane is used as a reducing agent, it is preferable to use an anhydrous solvent such as diethyl ether, tetrahydrofuran, diglyme, etc.

The reduction of the compound (32) or the compound (35) may also be carried out by catalytic hydrogenation in the presence of a catalyst in a suitable solvent. The solvent includes, for example, water, acetic acid, alcohols (e.g. methanol, ethanol, isopropanol, etc.), hydrocarbons (e.g. hexane, cyclohexane, etc.), ethers (e.g. dioxane, tetrahydrofuran, diethyl ether, ethylene glycol dimethyl ether, etc.), esters (e.g. ethyl acetate, methyl acetate, etc.), aprotic polar solvents (e.g. dimethylformamide, etc.), etc. The catalyst includes, for example, palladium, palladium-black, palladium-carbon, platinum, platinum oxide, copper chromite, Raney-nickel, etc. The catalyst is usually used in an amount of 0.02–1 time by weight as much as the amount of the compound (32) or the compound (35). The reaction is usually carried out at a temperature from −20° C. to about 150° C., preferably at a temperature from 0° C. to about 100° C., under 1 atm to 10 atms of hydrogen gas for 0.5 hour to about 10 hours.

Reaction Scheme-11

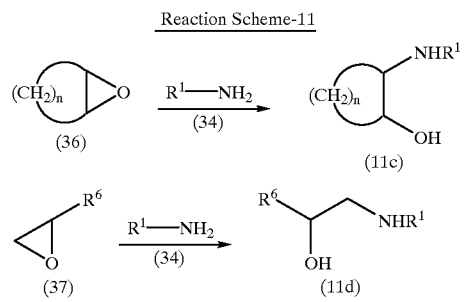

wherein $R^1$ is the same as defined above, n is an integer of 1 to 6, and $R^6$ is a lower alkyl group.

The reaction of the compound (36) and the compound (34), and the reaction of the compound (37) and the compound (34) are carried out in a suitable solvent. The solvent may be the same solvents for the reaction of the compound (2) and the compound (3) in the above Reaction Scheme-1. The compound (34) is usually used at least in an equimolar amount, preferably in an amount of 1 mole to 1.5 mole, to 1 mole of the compound (36) or the compound (37). The reaction is usually carried out at a temperature from room temperature to 150° C., preferably at a temperature from room temperature to about 100° C., for 1 hour to about 10 hours.

Reaction Scheme-12

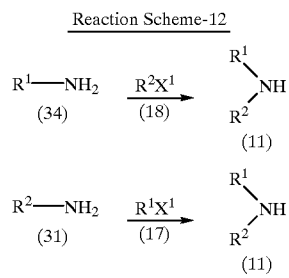

wherein $R^1$, $R^2$ and $X^1$ are the same as defined above.

The reaction of the compound (34) and the compound (18), and the reaction of the compound (31) and the compound (17) are carried out under the same conditions as those in the reaction of the compound (4) and the compound (5) in the above Reaction Scheme-2.

Reaction Scheme-13

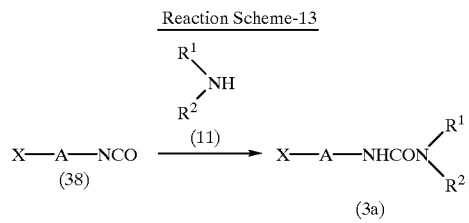

wherein $R^1$, $R^2$, X and A are the same as defined above.

The reaction of the compound (38) and the compound (11) is carried out in the same solvent as in the reaction of the compound (4) and the compound (5) in the above Reaction Scheme-2, at a temperature from room temperature to 100° C., preferably at a temperature from room temperature to about 70° C., for 0.5 hour to about 5 hours. The compound (11) is usually used at least in an amount of 1 mole to 2 moles, preferably in an amount of 1 mole to 1.5 mole, to 1 mole of the compound (38).

Reaction Scheme-14

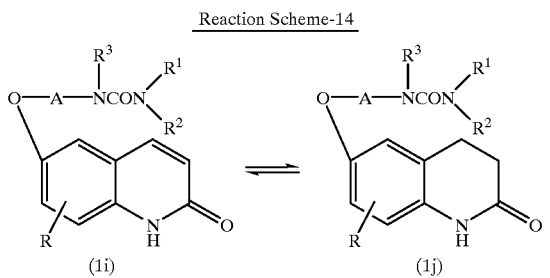

wherein R, $R^1$, $R^2$, $R^3$ and A are the same as defined above.

The reduction of the compound (1i) to convert into the compound (1j) is carried out under conventional catalytic reduction conditions. The catalyst includes, for example, metals such as palladium, palladium-carbon, platinum, Raney-nickel, etc. The catalyst is used in a conventional catalytic amount. The solvent includes, for example, alcohols (e.g. methanol, ethanol, isopropanol, etc.), ethers (e.g. dioxane, tetrahydrofuran, etc.), aliphatic hydrocarbons (e.g. hexane, cyclohexane, etc.), esters (e.g. ethyl acetate, etc.), fatty acids (e.g. acetic acid, etc.), etc. The reduction is carried out either under atmospheric pressure, or under pressure, for example, under a pressure from atmospheric pressure to about 20 kg/cm², preferably under a pressure from atmospheric pressure to 10 kg/cm², at a temperature from 0° C. to 150° C., preferably at a temperature from room temperature to about 100° C.

The de-hydrogenation reaction of the compound (1j) to convert into the compound (1i) is carried out by using an oxidizing agent in a suitable solvent. The oxidizing agent includes, for example, benzoquinones (e.g. 2,3-dichloro-5,6-dicyanobenzoquinone, chloranil (2,3,4,5-tetrachlorobenzoquinone), etc.), halogenating agents (e.g. N-bromosuccinimide, N-chlorosuccinimide, bromine, etc.), catalysts (e.g. selenium dioxide, palladium-carbon, palladium-black, palladium oxide, Raney-nickel, etc.), and the like. The amounts of the benzo-quinones and the halogenating agent are not critical, but it is usually in the range of 1 mole to 15 moles, preferably in the range of 1 mole to 10 moles, to 1 mole of the compound (1j). In case of using a catalyst, it is used in a conventional catalytic amount. The solvent includes, for example, ethers (e.g. dioxane, tetrahydrofuran, methoxyethanol, dimethoxyethane, etc.), aromatic hydrocarbons (e.g. benzene, toluene, xylene, cumene, etc.), halogenated hydrocarbons (e.g. dichloromethane, dichloroethane, chloroform, carbon tetrachloride, etc.), alcohols (e.g. butanol, amyl alcohol, hexanol, etc.), polar protic solvents (e.g. acetic acid, etc.), polar aprotic solvents (e.g. dimethylformamide, dimethyl sulfoxide, hexamethylphosphoric triamide, etc.), etc. The reaction is usually carried out at a temperature from room temperature to about 300° C., preferably at a temperature from room temperature to about 200° C., for 1 hour to 40 hours.

Reaction Scheme-15

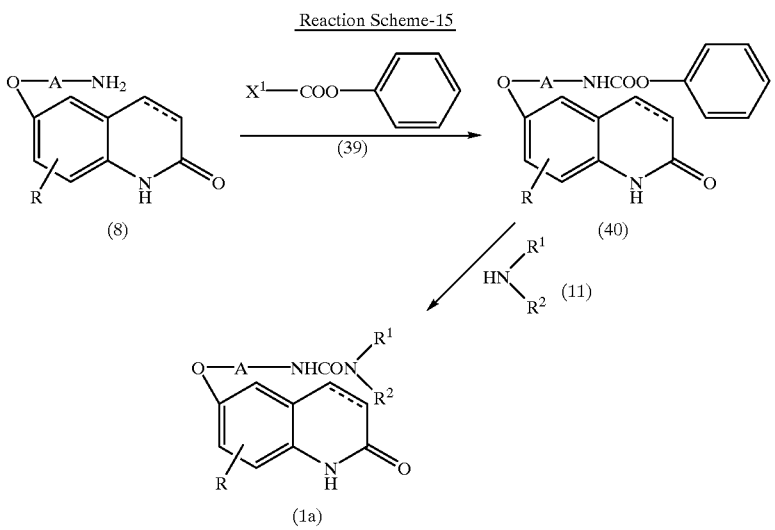

wherein R, $R^1$, $R^2$, $X^1$ and A are the same as defined above.

The reaction of the compound (8) and the compound (39) is carried out in the presence of a basic compound in a suitable solvent. The solvent and the basic compound are the same ones as those in the reaction of the compound (4) and the compound (5) in the above Reaction Scheme-2. The reaction is usually carried out at a temperature from −20° C. to 50° C., preferably at a temperature from −20° C. to room temperature, for 30 minutes to about 5 hours. The compound (39) is used at least in an equimolar amount, preferably in an amount of 1 mole to 2 moles, to 1 mole of the compound (8). The reaction of the compound (40) and the compound (11) is carried out under the same conditions as those in the reaction of the compound (10) and the compound (11) in the above Reaction Scheme-3.

Reaction Scheme-16

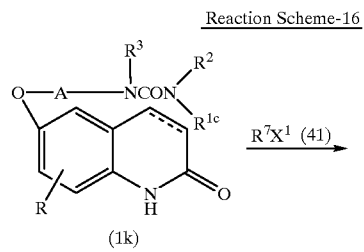

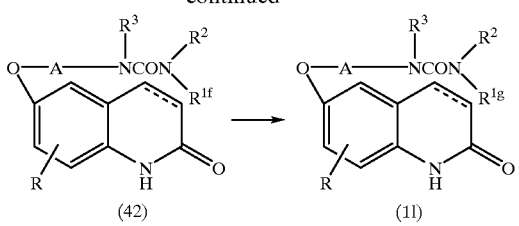

wherein R, $R^2$, $R^3$, $R^{1c}$, A, $X^1$ and the bond between 3- and 4-positions of the carbostyril nucleus are the same as defined above, $R^{1f}$ is a cycloalkyl group having a tetrahydropyranyloxy-lower alkoxy substituent, $R^7$ is a tetrahydropyranyloxy-lower alkyl group, and $R^{1g}$ is a cycloalkyl group having a hydroxy-substituted lower alkoxy substituent.

The reaction of the compound (1k) and the compound (41) is carried out under the same conditions as those in the reaction of the compound (1g) and the compound (19) in the above Reaction Scheme-6.

The reaction of converting the compound (42) into the compound (11) is carried out under the same conditions as those in the hydrolysis of the compound (1h) of the above Reaction Scheme-6. The reaction may be preferably carried out in the presence of an acid.

Reaction Scheme-17

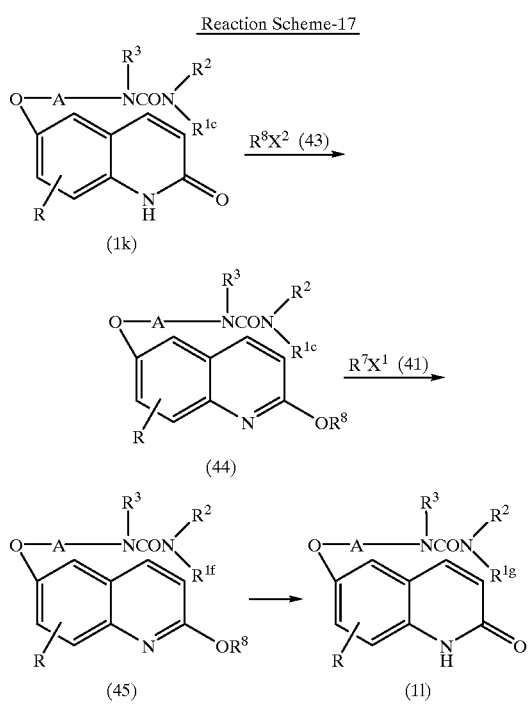

wherein R, $R^2$, $R^3$, $R^{1c}$, $R^{1f}$, $R^{1g}$, $R^7$, A, $X^1$ and $X^2$ are the same as defined above, and $R^8$ is a lower alkoxy-lower alkyl group.

The reaction of the compound (1k) and the compound (43) is carried out under the same conditions as those in the reaction of the compound (1g) and the compound (19) in the above Reaction Scheme-6.

The reaction of the compound (44) and the compound (41) is carried out under the same conditions as those in the reaction of the compound (1g) and the compound (19) in the above Reaction Scheme-6.

The reaction of converting the compound (45) into the compound (11) is carried out under the same conditions as those in the reaction of converting the compound (42) into the compound (11) in the above Reaction Scheme-16.

Reaction Scheme-18

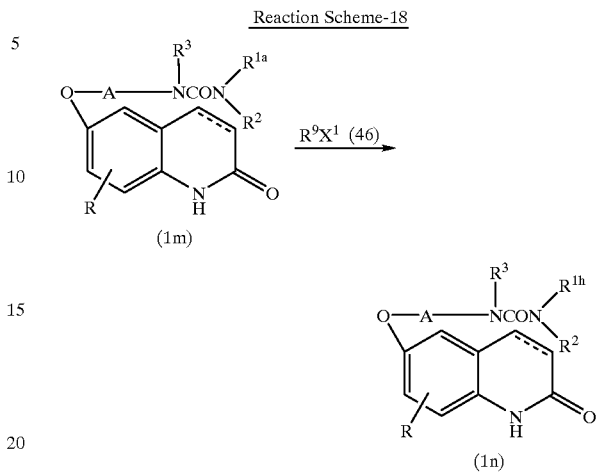

wherein R, $R^2$, $R^3$, $R^{1a}$, A, $X^1$ and the bond between 3- and 4-positions of the carbostyril nucleus are the same as defined above, $R^{1h}$ is a lower alkyl group having a substituent selected from a lower alkoxy group and a phenyl-lower alkoxy group, and $R^9$ is a lower alkyl group or a phenyl-lower alkyl group.

The reaction of the compound (1m) and the compound (46) is carried out under the same conditions as those in the reaction of the compound (1e) and the compound (19) in the above Reaction Scheme-6.

Reaction Scheme-19

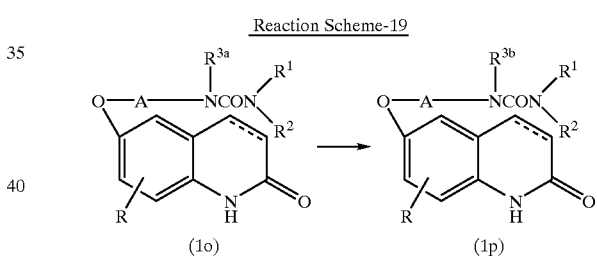

wherein R, $R^1$, $R^2$, A and the bond between 3- and 4-positions of the carbostyril nucleus are the same as defined above, $R^{3a}$ is a lower alkenyl group, and $R^{3b}$ is a lower alkyl group.

The reduction reaction of the compound (1o) to convert into the compound (1p) is carried out under the same conditions as those in the reaction of converting the compound (27) into the compound (8) by using a catalyst in the above Reaction Scheme-7.

Reaction Scheme-20

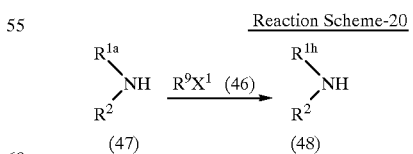

wherein $R^{1a}$, $R^2$, $R^{1h}$, $R^9$ and $X^1$ are the same as defined above.

The reaction of the compound (47) and the compound (46) is carried out under the same conditions as those in the reaction of the compound (1e) and the compound (19) in the above Reaction Scheme-6.

Reaction Scheme-21

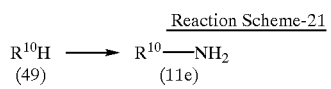

wherein $R^{10}$ is an amino group having optionally a substituent selected from a lower alkyl group and a cycloalkyl group.

The reaction of converting the compound (49) into the compound (11e) is carried out by reacting the compound (49) with a metal nitrite such as sodium nitrite, potassium nitrite, in a suitable solvent such as water, in the presence of an acid, and then reacting the product with formamidine sulfinic acid in the presence of a basic compound in a suitable solvent.

The acid used in the reaction with the metal nitrite is, for example, hydrochloric acid, hydrobromic acid, sulfuric acid, tetrafluoroboric acid, hexafluorophosphoric acid, etc. The reaction is usually carried out at a temperature from room temperature to 150° C., preferably at a temperature from room temperature to about 100° C., for 1 hour to about 5 hours. The metal nitrite is usually used in an amount of 1 mole to 5 moles, preferably in an amount of 1 mole to 3 moles, to 1 mole of the compound (49).

The solvent and the basic compound used in the reaction with the formamidine sulfinic acid are the same solvents and the same basic compounds as those in the reaction of the compound (4) and the compound (5) in the above Reaction Scheme-2. The reaction is usually carried out at a temperature from room temperature to 150° C., preferably at a temperature from room temperature to about 100° C., for one hour to about 5 hours. The formamidine sulfinic acid is usually used in an amount of 1 mole to 5 moles, preferably in an amount of 1 mole to 3 moles, to 1 mole of the compound (49).

The compound of the formula (11) wherein at least one of $R^1$ and $R^2$ is a lower alkyl group having a hydroxy substituent or a cycloalkyl group having a hydroxy substituent can be converted into an optically active compound (11) by reacting with an optically active compound in the presence of an acid in a suitable solvent to give an adduct compound wherein a hydroxy group of the formula (11) is combined with the optically active compound, followed by hydrolyzing the resulting compound, or by subjecting the compound (11) to optical resolution by reacting with an optically active compound in a suitable solvent. The solvent includes, for example, alcohols (e.g. methanol, ethanol, isopropanol, etc.), aromatic hydrocarbons (e.g. benzene, toluene, xylene, etc.), halogenated hydrocarbons (e.g. dichloromethane, dichloroethane, chloroform, carbon tetrachloride, etc.), ethers (e.g. diethyl ether, dioxane, tetrahydrofuran, diglyme, etc.), saturated hydrocarbons (e.g. n-hexane, n-heptane, cyclohexane, etc.), ketones (e.g. acetone, methyl ethyl ketone, etc.), polar solvents (e.g. dimethylformamide, dimethyl sulfoxide, hexamethylphosphoric triamide, acetonitrile, etc.), or a mixture thereof. The acid includes, for example, mineral acids (e.g. hydrochloric acid, sulfuric acid, hydrobromic acid, etc.), organic acids (e.g. formic acid, acetic acid, methanesulfonic acid, p-toluenesulfonic acid, etc.), etc. The optically active compound may be optically active acids, for example, (+)- and (−)-tartaric acid, (+)- and (−)-di-p-toluoyltartaric acid, (+)- and (−)-malic acid, (+)- and (−)-mandelic acid, D- or L-camphor-10-sulfonic acid, etc. The optically active compound is usually used at least in an equimolar amount, preferably in an amount of 1 mole to 1.5 mole, to 1 mole of the starting compound. The reaction is usually carried out at a temperature from room temperature to 200° C., preferably at a temperature from room temperature to about 150° C., for one hour to about 10 hours. The subsequent hydrolysis is carried out under the same conditions as those in the hydrolysis of the compound (1f) in the above Reaction Scheme-6.

The optical resolution of the compound (11) is carried out, for example, by reacting with an optically active compound in a suitable solvent to give a salt of the compound (11), fractional crystallization of the salt, and then followed by desaltation of the resulting optically active salt of the compound (11). The optically active compound to be used for salt-formation of the compound (11) may be any compound being capable to form a salt with the compound (11), for example, the above mentioned optically active compounds. The solvent may be any solvent which is conventionally used in a conventional optical resolution, for example, the same solvents as those for the above reaction of the hydroxy group of the compound (11) and the optically active compound. The optically active compound is usually used in an amount of 0.3 mole to 3 moles, preferably in an amount of 0.5 mole to 1 mole, to 1 mole of the compound (11). The reaction is usually carried out at a temperature from 0° C. to about 100° C., preferably at a temperature from room temperature to about 50° C.

The fractional crystallization of the salt of the compound (11) is carried out by a conventional method to isolate the salt of the optically active compound (11).

The subsequent desaltation of the salt of the optically active compound (11) is carried out in the presence of a basic compound in a suitable solvent. The solvent includes, for examples, in addition to water, the same solvents as those in the above salt-formation reaction. The basic compound includes, for example, inorganic bases such as sodium hydroxide, sodium carbonate, potassium hydroxide, potassium carbonate, potassium hydrogen carbonate, sodium hydrogen carbonate, etc. The basic compound may be used in a largely excess amount.

Among the carbostyril derivatives (1) of the present invention, the compounds having an acidic group can easily be converted into salts by treating with a pharmaceutically acceptable basic compound. The basic compound includes, for example, sodium hydroxide, potassium hydroxide, calcium hydroxide, sodium carbonate, potassium hydrogen carbonate, etc.

The compounds of the present invention obtained in the above processes can easily be isolated and purified by conventional isolation methods. The isolation methods are, for example, extraction with a solvent, dilution method, recrystallization method, column chromatography, preparative thin layer chromatography, and the like.

The present invention also includes geometrical isomers, optical isomers, as well.

The desired compounds (1) of the present invention and salts thereof are used in the form of a conventional pharmaceutical preparation. The preparation is prepared by using conventional diluents or carriers such as fillers, thickening agents, binders, wetting agent, disintegrators, surfactants, lubricants, etc. The pharmaceutical preparations can be selected from various forms in accordance with the desired utilities, and the representative forms are tablets, pills, powders, solutions, suspensions, emulsions, granules, capsules, suppositories, injections (solutions, suspensions, etc.), etc. In order to form in tablets, there are used conventional carriers such as vehicles (e.g. lactose, white sugar, sodium chloride, glucose, urea, starch, calcium carbonate, kaolin, crystalline cellulose, silicic acid, etc.), binders (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium alginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium base, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc.), etc. Moreover, the tablets may also be in the form of a conventional coated tablet, such as sugar-coated tablets, gelatin-coated tablets, enteric coated tablets, film coating tablets, or double or multiple layer tablets. In the preparation of pills, the carriers include vehicles (e.g. glucose, lactose, starches, cacao butter, hydrogenated vegetable oils, kaolin, talc, etc.), binders (e.g. gum arabic powder, tragacanth powder, gelatin, ethanol, etc.), disintegrators (e.g. laminaran, agar, etc.), etc. In the preparation of suppositories, the carriers include, for example, polyethylene glycol, cacao butter, higher alcohols, higher alcohol esters, gelatin, semi-synthetic glycerides, etc. Capsules can be prepared by charging a mixture of the compound of the present invention and the above carriers into hard gelatin capsules or soft capsules in usual manner. In the preparation of injections, the solutions, emulsions and suspensions are sterilized and are preferably made isotonic with the blood. In the preparation of these solutions, emulsions and suspensions, there are used conventional diluents such as water, ethyl alcohol, propylene glycol, ethoxylated isostearyl alcohol, polyoxylated isostearyl alcohol, polyoxyethylene sorbitan fatty acid esters, etc. In this case, the pharmaceutical preparations may also be incorporated with sodium chloride, glucose, or glycerin in an amount sufficient to make them isotonic, and may also be incorporated with conventional solubilizers, buffers, anesthetizing agents. Besides, the pharmaceutical preparations may optionally be incorporated with coloring agents, preservatives, perfumes, flavors, sweeting agents, and other medicaments, if required.

The amount of the desired compound (1) of the present invention to be incorporated into the pharmaceutical preparation is not specified but may be selected from a broad range, but usually, it is preferably in the range of 1 to 70 % by weight, more preferably 1 to 30% by weight.

The pharmaceutical preparation containing as an active ingredient the compounds (1) of the present invention and a salt thereof may be administered by any method, and suitable method for administration may be determined in accordance with various forms of preparations, ages, sexes and other conditions of the patients, the degree of severity of diseases, etc. For example, tablets, pills, solutions, suspensions, emulsions, granules and capsules are administered orally. The injections are intravenously administered alone or together with a conventional auxiliary liquid (e.g. glucose, amino acid solutions, etc.), and further are optionally administered alone in intramuscular, intracutaneous, subcutaneous, or intraperitoneal route, if required. Suppositories are administered in intrarectal route.

The dosage of the pharmaceutical preparation of the present invention may be selected in accordance with the usage, ages, sexes and other conditions of the patients, the degree of severity of the diseases, etc., but it is usually in the range of about 0.1 to 10 mg of the active compound (1) of the present invention per 1 kg of body weight of the patient per day. The active compound is preferably contained in an amount of about 1 to about 200 mg per the dosage unit.

BEST MODE FOR CARRYING OUT THE INVENTION

The present invention is illustrated in more detail by the following Preparations of pharmaceutical preparations, Reference Examples of processes for preparing the starting compounds to be used for preparing the desired compounds (1) of the present invention, and Examples of processes for preparing the desired compounds (1), and Pharmacological Experiments of the activities of the desired compounds of the present invention.

PREPARATION 1

Preparation of tablets:

| Components | Amount |
|---|---|
| 6-{3-[3-(trans-2-Hydroxycyclohexyl)-3-cyclopropylureido]propoxy}carbostyril | 5 g |
| Lactose (Japanese Pharmacopeia) | 50 g |
| Corn starch (Japanese Pharmacopeia) | 25 g |
| Crystalline cellulose (Japanese Pharmacopeia) | 25 g |
| Methyl cellulose (Japanese Pharmacopeia) | 1.5 g |
| Magnesium stearate (Japanese Pharmacopeia) | 1 g |

The active compound of the present invention, lactose, corn starch and crystalline cellulose are mixed. The mixture is granulated with a 5% aqueous solution of methyl cellulose. The resulting particles are passed through a screen (200 mesh) and dried carefully. The mixture is tabletted by a conventional manner to give 1000 tablets.

PREPARATION 2

Preparation of capsules:

| Components | Amount |
|---|---|
| 6-[3-(1,3-Dimethyl-3-cyclohexylureido)-propoxy]carbostyril | 10 g |
| Lactose (Japanese Pharmacopeia) | 80 g |
| Starch (Japanese Pharmacopeia) | 30 g |
| Talc (Japanese Pharmacopeia) | 5 g |
| Magnesium stearate (Japanese Pharmacopeia) | 1 g |

The above components are mixed, pulverized and stirred well. The resulting uniform mixture is charged into gelatin capsules for oral administration of a desired size to give 1000 capsules.

PREPARATION 3

Preparation of injection preparation:

| Components | Amount |
|---|---|
| 6-{3-Cyclohexyl-[3-(2-acetyloxybutyl)ureido]-propoxy}carbostyril | 1 g |
| Polyethylene glycol (molecular weight: 4000) (Japanese Pharmacopeia) | 0.3 g |
| Sodium chloride (Japanese Pharmacopeia) | 0.9 g |
| Polyoxyethylene sorbitan monooleate | 0.4 g |

| Components | Amount |
| --- | --- |
| (Japanese Pharmacopeia) | |
| Sodium metabisulfite | 0.1 g |
| Methyl-paraben (Japanese Pharmacopeia) | 0.18 g |
| Propyl-paraben (Japanese Pharmacopeia) | 0.02 g |
| Distilled water for injection | 100 ml |

The above parabens, sodium metabisulfite and sodium chloride are dissolved in distilled water of half volume of the above with stirring at 80° C. The solution thus obtained is cooled to 40° C., and the active compound of the present invention and further polyethylene glycol and polyoxyethylene sorbitan monooleate are dissolved in the above solution. To the solution is added distilled water for injection to adjust to the desired volume, and the solution is sterilized by filtering with an appropriate filter paper to give an injection preparation.

REFERENCE EXAMPLE 1

A suspension of 6-hydroxycarbostyril (300 g) and potassium carbonate (308 g) in dimethylformamide (2 liters) is heated with stirring at 70–80° C. for one hour. To the suspension is added N-(3-bromopropyl)phthalimide (498 g), and the mixture is further stirred at the same temperature for 9 hours. The reaction solution is poured into ice-water, and the precipitated crystals are collected by filtration, washed successively with water, ethanol and diethyl ether, and dried to give 6-(3-phthalimidopropoxy)carbostyril (410 g) as a white powder.

$^1$H-NMR (DMSO-d$_6$) δ ppm: 2.00–2.18 (2H, m), 3.78 (2H, t, J=6 Hz), 4.04 (2H, t, J=6 Hz), 6.47 (1H, d, J=9.5 Hz), 6.97 (1H, dd, J=2.5 Hz, J=9 Hz), 7.10 (1H, d, J=2.5 Hz), 7.18 (1H, d, J=9 Hz), 7.78 (1H, d, J=9.5 Hz), 7.75-7.94 (5H, m), 12.08 (1H, brs)

REFERENCE EXAMPLE 2

To a suspension of 6-(3-phthalimidopropoxy)carbostyril (300 g) in ethanol (3 liters) is added hydrazine monohydrate (46 g), and the mixture is refluxed for 8 hours. After the mixture is allowed to cool, the precipitated crystals are collected by filtration, suspended in water, and the suspension thus obtained is acidified with conc. hydrochloric acid, and stirred for one hour. The insoluble materials are removed by filtration, and the filtrate is concentrated under reduced pressure to remove the solvent. The residue is neutralized to pH 7 with a 15% aqueous sodium hydroxide solution. The precipitated crystals are collected by filtration, and washed successively with ethanol and diethyl ether, and dried to give 6-(3-aminopropoxy)carbostyril (140 g) as a white powder.

$^1$H-NMR (DMSO-d$_6$) δ ppm: 2.02–2.20 (2H, m), 2.88–3.08 (2H, m), 4.12 (2H, t, J=6 Hz), 6.52 (1H, d, J=9.5 Hz), 7.18 (1H, dd, J=2.5 Hz, J=9 Hz), 7.24 (1H, d, J=2.5 Hz), 7.32 (1H, d, J=9 Hz), 7.86 (1H, d, J=9.5 Hz), 8.15–8.50 (3H, m), 11.75 (1H,brs)

REFERENCE EXAMPLE 3

To a solution of N,N-carbonyldiimidazole (139 g) and imidazole (117 g) in dimethylsulfoxide (2 liters) is added with stirring 6-(3-aminopropoxy)carbostyril (200 g) in portions under ice-cooling. The mixture is further stirred at room temperature for one day, and poured into ice-water. The precipitated crystals are collected by filtration, and washed with water. The crystals thus obtained are further washed successively with ethanol and diethyl ether, and dried to give 6-[3-(1-imidazolyl)carbonylaminopropoxy]carbostyril (162 g) as a white powder.

$^1$H-NMR (DMSO-d$_6$) δ ppm: 1.94–2.18 (2H, m), 3.30–3.63 (2H, m), 4.09 (2H, t, J=6 Hz), 6.51 (1H, d, J=9.5 Hz), 7.05 (1H, s), 7.15 (1H, dd, J=2.5 Hz, J=9 Hz), 7.22 (1H, d, J=2.5 Hz), 7.26 (1H, d, J=9 Hz), 7.69 (1H, s), 7.84 (1H, d, J=9.5 Hz), 8.26 (1H, s), 8.61 (1H, t, J=5.3 Hz), 11.68 (1H, brs)

REFERENCE EXAMPLE 4

To a suspension of 6-hydroxycarbostyril (50 g) and 1-bromo-3-chloropropane (120 ml) in dimethylformamide (600 ml) is added potassium carbonate (65 g) in portions at room temperature. The mixture is stirred at room temperature for three days, and the insoluble materials are collected by filtration and washed with n-hexane. The resulting crystals are further washed successively with water, acetone and n-hexane, and dried to give 6-(3-chloropropoxy)carbostyril (50.7 g) as a white powder.

$^1$H-NMR (DMSO-d$_6$) δ ppm: 2.19 (2H, quint, J=6 Hz), 3.81 (2H, t, J=6 Hz), 4.11 (2H, t, J=6 Hz), 6.50 (1H, d, J=9.5 Hz), 7.16 (1H, dd, J=2.5 Hz, J=9 Hz), 7.20–7.32 (2H, m), 7.84 (1H, d, J=9.5 Hz), 11.60 (1H, br)

REFERENCE EXAMPLE 5

A suspension of 6-(3-chloropropoxy)carbostyril (170 g) and sodium iodide (129.5 g) in dimethylformamide (1.7 liter) is heated with stirring at 60° C. for one hour. To the mixture is added potassium phthalimide (159 g), and the mixture is heated with stirring at 70° C. for 6 hours. After the mixture is allowed to cool, the precipitated crystals are collected by filtration, and washed with water. The mixture is further washed successively with ethanol and diethyl ether, and dried to give 6-(3-phthalimidopropoxy)carbostyril (222 g) as a white powder.

$^1$H-NMR (DMSO-d$_6$) δ ppm: 2.00–2.18 (2H, m), 3.78 (2H, t, J=6 Hz), 4.04 (2H, t, J=6 Hz), 6.47 (1H, d, J=9.5 Hz), 6.97 (1H, dd, J=2.5 Hz, J=9 Hz), 7.10 (1H, d, J=2.5 Hz), 7.18 (1H, d, J=9 Hz), 7.78 (1H, d, J=9.5 Hz), 7.75–7.94 (SH, m), 12.08 (1H, brs)

REFERENCE EXAMPLE 6

A suspension of 6-(3-chloropropoxy)carbostyril (100 g) and sodium azide (33 g) in dimethylformamide is refluxed at 80° C. for 4 hours. After the mixture is allowed to cool, to the mixture is added ice-water, and the precipitated crystals are collected by filtration, washed with diethyl ether, and dried to give 6-(3-azidopropoxy)carbostyril (100 g) as a white powder.

$^1$H-NMR (DMSO-d$_6$) δ ppm: 2.00 (2H, quint, J=6 Hz), 3.53 (2H, t, J=6 Hz), 4.06 (2H, t, J=6 Hz), 6.51 (1H, d, J=9.5 Hz), 7.12–7.35 (3H, m), 7.85 (1H, d, J=9.5 Hz), 11.69 (1H, s)

REFERENCE EXAMPLE 7

To a solution of 6-(3-azidopropoxy)carbostyril (17.5 g) in a mixture of ethyl acetate-methanol (1:1, 700 ml) is added 10% palladium-carbon (1.75 g), and the mixture is subjected to hydrogenation at room temperature under atmospheric pressure. After the reaction is complete, the catalyst is removed by filtration, and the filtrate is concentrated under reduced pressure to remove the solvent. The resulting residue is washed with diethyl ether to give 6-(3-aminopropoxy)carbostyril (14.7 g) as a white powder.

$^1$H-NMR (DMSO-$d_6$) δ ppm: 2.02–2.20 (2H, m), 2.88–3.08 (2H, m), 4.12 (2H, t, J=6 Hz), 6.52 (1H, d, J=9.5 Hz), 7.18 (1H, dd, J=2.5 Hz, J=9 Hz), 7.24 (1H, d, J=2.5 Hz), 7.32 (1H, d, J=9 Hz), 7.86 (1H, d, J=9.5 Hz), 8.15–8.50 (3H, m), 11.75 (1H, brs)

REFERENCE EXAMPLE 8

To a suspension of lithium aluminum hydride (1.9 g) in anhydrous tetrahydrofuran (50 ml) is added dropwise with stirring a solution of 6-(3-azidopropoxy)carbostyril (10 g) in anhydrous tetrahydrofuran (200 ml) under ice-cooling. The mixture is stirred at room temperature for one hour, and thereto are added dropwise water (2 ml), a 15% aqueous sodium hydroxide solution (2 ml) and water (6 ml). The insoluble materials are collected by filtration, and added to a mixture of chloroform-methanol (8: 1). The mixture is heated, and then cooled. The insoluble material are removed by filtration. The filtrate is concentrated under reduced pressure to remove the solvent, and thereto is added diethyl ether. The precipitated crystals are collected by filtration to give 6-(3-aminopropoxy)carbostyril (6.2 g) as a white powder.

$^1$H-NMR (DMSO-$d_6$) δ ppm: 2.02–2.20 (2H, m), 2.88–3.08 (2H, m), 4.12 (2H, t, J=6 Hz), 6.52 (1H, d, J=9.5 Hz), 7.18 (1H, dd, J=2.5 Hz, J=9 Hz), 7.24 (1H, d, J=2.5 Hz), 7.32 (1H, d, J=9 Hz), 7.86 (1H, d, J=9.5 Hz), 8.15–8.50 (3H, m), 11.75 (1H, brs)

REFERENCE EXAMPLE 9

Cyclohexene oxide (143 ml) and cyclopropylamine (82 g) are dissolved in methanol (1 liter), and the mixture is refluxed for 5 hours. The mixture is concentrated under reduced pressure to remove the solvent, and the resulting residue is distilled under reduced pressure to give trans-N-(2-hydroxycyclohexyl)-N-cyclopropylamine (126 g) as a colorless oil.

B.p. 79–85° C./0.5–1 mmHg

REFERENCE EXAMPLE 10

To toluene (1.5 liter) are added trans-N-(2-hydroxycyclohexyl)-N-cyclo-propylamine (150 g), (R)-(-)-mandelic acid (147 g) and p-toluenesulfonic acid monohydrate (203 g), and the mixture is refluxed for 6 hours during which the generated water is removed by a Dean-stark apparatus. The mixture is poured into ice-water, and thereto is added an aqueous solution of sodium hydrogen carbonate (98 g), and the mixture is stirred for one hour. The toluene layer is collected, and the aqueous layer is extracted with ethyl acetate. The organic layers are combined, washed with a saturated aqueous sodium chloride solution, and dried over anhydrous sodium sulfate. The mixture is concentrated under reduced pressure to remove the solvent, and the residue is purified by silica gel column chromatography (solvent; n-hexane:ethyl acetate=3:1→1:1), and crystallized from ethyl acetate-n-hexane (1:1). The resultant is further recrystallized from ethyl acetate-n-hexane (1:2) to give (S,S)-(+)-trans-N-(2-mandeloyloxycyclohexyl)-N-cyclopropylamine (25 g) as colorless rods.

M.p. 102–103° C.

REFERENCE EXAMPLE 11

(S)-(+)-Mandelic acid is treated in the same manner as in Reference Example 10 to give (R,R)-(-)-trans-N-(2-mandeloyloxycyclohexyl)-N-cyclopropylamine, which is recrystallized from ethyl acetate-n-hexane (1:2) to give colorless rods.

M.p. 101–103° C.

REFERENCE EXAMPLE 12

To a suspension of (S,S)-(+)-trans-N-(2-mandeloyloxycyclohexyl)-N-cyclopropylamine (25 g) in methanol (250 ml) is added dropwise with stirring a 3N aqueous potassium hydroxide solution (87 ml) at room temperature. The mixture is further stirred at room temperature for 0.5 hour, and extracted with methylene chloride. The extract is washed successively with water and a saturated aqueous sodium chloride solution, and dried over anhydrous sodium sulfate. The resultant is concentrated under reduced pressure, and distilled under reduced pressure to give (S,S)-(+)-trans-N-(2-hydroxycyclohexyl)-N-cyclopropylamine (13.4 g) as a colorless oil.

B.p. 87° C./2 mmHg

After being allowed to stand, the above product is crystallized as colorless rods.

M.p. 43–45° C.

$[\alpha]_D^{24}$=+59.4° (c=1.0, methanol)

REFERENCE EXAMPLE 13

(R,R)-(-)-trans-N-(2-Mandeloyloxycyclohexyl)-N-cyclopropylamine is treated in the same manner as in Reference Example 12 to give (R,R)-(-)-trans-N-(2-hydroxycyclohexyl)-N-cyclopropylamine as a colorless oil.

B.p. 79° C./0.5 mmHg

The above product is allowed to stand to give colorless rods.

M.p. 43–45° C.

$[\alpha]_D^{24}$=-59.3° (c=1.0, methanol)

REFERENCE EXAMPLE 14

1-Amino-2-butanol (120 g) is added dropwise into a solution of cyclohexanone (132 g) in ethanol (600 ml) at room temperature, and the mixture is stirred at room temperature for one day. To the reaction solution is added 10% palladium-carbon (6 g), and the mixture is subjected to catalytic hydrogenation at 60° C. under 4 atms of hydrogen gas. The catalyst is removed by filtration, and the filtrate is concentrated under reduced pressure, and distilled under reduced pressure to give N-(2-hydroxybutyl)-N-cyclohexylamine (223 g) as a colorless oil.

B.p. 87–93° C./0.35–0.4 mmHg

REFERENCE EXAMPLE 15

To methanol (200 ml) are added 1,2-epoxybutane (72.2 g) and cyclohexylamine (99.2 g), and the mixture is refluxed for 6 hours. The mixture is concentrated under reduced pressure to remove the solvent to give N-(2-hydroxybutyl)-N-cyclohexylamine (105 g) as a colorless oil.

B.p. 87–93° C./0.35–0.4 mmHg

REFERENCE EXAMPLE 16

To a solution of triphosgene (4.35 g) in toluene (70 ml) is added dropwise N-methylcyclohexylamine (5 g). To the mixture is added dropwise pyridine (3.5 g), and the mixture is refluxed for 4 hours. The mixture is allowed to cool, and the organic layer is separated, washed with 0.1 N hydrochloric acid, dried over anhydrous magnesium sulfate, and concentrated under reduced pressure to remove the solvent to give N-methyl-N-cyclohexylaminocarbonyl chloride (7.62 g) as a colorless oil.

¹H-NMR (CDCl₃) δ ppm: 1.00–2.00 (10H, m), 2.9 and 3.1 (all 3H, each s), 4.10 (1H, m)

REFERENCE EXAMPLE 17

6-(3-Chloropropoxy)carbostyril (20 g) is added into a 40% solution of methylamine in methanol (200 ml), and the mixture is heated with stirring at 100° C. overnight in a sealed tube. The mixture is concentrated under reduced pressure to remove the solvent, and the precipitated crystals are washed with a mixture of chloroform-diethyl ether, purified by silica gel column chromatography (solvent; methylene chloride:methanol:aqueous ammonia=50:10:1), and recrystallized from chloroform-diethyl ether to give 6-(3-methylaminopropoxy)carbostyril (15.4 g).

M.p. 160–161.5° C.

REFERENCE EXAMPLE 18

Using the corresponding starting compounds, the following compounds are obtained in the same manner as in Reference Example 17.
(1) 6-(3-Ethylaminopropoxy)carbostyril
¹H-NMR (DMSO-d₆) δ ppm: 1.08 (3H, t, J=7 Hz), 1.85–2.05 (2H, m), 2.72 (2H, q, J=7 Hz), 2.83 (2H, t, J=7 Hz), 4.06 (2H, t, J=6 Hz), 6.50 (1H, d, J=9.5 Hz), 7.10–7.30 (3H, m), 7.84 (1H, d, J=9.5 Hz)
(2) 6-(3-Allylaminopropoxy)carbostyril
¹H-NMR (DMSO-d₆) δ ppm: 2.15–2.20 (2H, m), 3.03 (2H, t, J=7 Hz), 3.59 (2H, d, J=6.5 Hz), 4.09 (2H, t, J=6 Hz), 5.35–5.55 (2H, m), 5.85–6.05 (1H, m), 6.50 (1H, d, J=9.5 Hz), 7.10–7.30 (3H, m), 7.84 (1H, d, J=9.5 Hz)

REFERENCE EXAMPLE 19

6-Hydroxycarbostyril (100 g) is added into phosphorus oxychloride (500 ml), and the mixture is refluxed for 5 hours. The mixture is concentrated under reduced pressure to remove the phosphorus oxychloride, and the residue thus obtained is dissolved in a small amount of chloroform, and then the mixture is poured into ice-water. The precipitated crystals are collected by filtration, washed successively with water, acetone and n-hexane, and dried to give 2-chloro-6-hydroxyquinoline hydrochloride (127 g).

¹H-NMR (DMSO-d₆) δ ppm: 7.50–7.70 (2H, m), 7.78 (11H, s), 7.95 (1H, d, J=9 Hz), 8.43 (1H, d, J=9 Hz)

REFERENCE EXAMPLE 20

To a suspension of 2-chloro-6-hydroxycarbostyril.hydrochloride (25 g) and potassium carbonate (38 g) in dimethylformamide (600 ml) is added N-(3-bromopropyl)phthalimide (31 g). The mixture is heated with stirring at 60° C. overnight. The reaction solution is poured into ice-water, and the precipitated crystals are collected by filtration, washed with water, and dried to give 2-chloro-6-(3-phthalimidopropoxy)quinoline (19.3 g) as a white powder.

¹H-NMR (DMSO-d₆) δ ppm: 2.10–2.25 (2H, m), 3.82 (2H, t, J=7 Hz), 4.17 (2H, t, J=6 Hz), 7.23 (1H, dd, J=3 Hz, J=9 Hz), 7.36 (1H, d, J=3 Hz), 7.52 (1H, d, J=9 Hz), 7.80 (1H, d, J=9 Hz), 7.85 (4H, s), 8.28 (1H, d, J=9 Hz)

REFERENCE EXAMPLE 21

To a suspension of 2-chloro-6-(3-phthalimidopropoxy) quinoline (9.0 g) in ethanol (250 ml) is added hydrazine.monohydrate (1.4 g), and the mixture is refluxed for 7.5 hours. The mixture is allowed to cool, and the precipitated crystals are collected by filtration, and suspended in water. The mixture is acidified with conc. hydrochloric acid, and stirred for one hour. The mixture is basified with a 10% aqueous potassium hydroxide solution, and extracted with chloroform. The extract is dried over anhydrous magnesium sulfate, and concentrated under reduced pressure to remove the solvent to give 2-chloro-6-(3-aminopropoxy)quinoline (4.7 g) as a white powder.

¹H-NMR (DMSO-d₆) δ ppm: 1.80–1.95 (2H, m), 2.74 (2H, t, J=7 Hz), 4.18 (2H, t, J=6 Hz), 7.40–7.50 (2H, m), 7.53 (1H, d, J=9 Hz), 7.86 (1H, d, J=10 Hz), 8.32 (1H, d, J=9 Hz)

REFERENCE EXAMPLE 22

To a solution of N,N-carbonyldimidazole (2.1 g) and imidazole (1.9 g) in chloroform (100 ml) is added dropwise with stirring a solution of 2-chloro-6-(3-aminopropoxy) quinoline (3 g) in chloroform (40 ml) at −10° C. The mixture is stirred at room temperature overnight, and thereto is added dropwise a solution of N-(2-hydroxybutyl)-N-cyclohexylamine (2.9 g) in chloroform (10 ml). The mixture is stirred at room temperature for one hour, and refluxed for 2.5 hours. The mixture is allowed to cool, and the chloroform layer is washed successively with diluted hydrochloric acid, water and a saturated aqueous sodium hydrogen carbonate solution, dried over anhydrous magnesium sulfate, and evaporated to remove the solvent to give 2-chloro-6-{3-[3-cyclohexyl-3-(2-hydroxybutyl)ureido]propoxy}quinoline (6.8 g) as a colorless oil.

¹H-NMR (DMSO-d₆) δ ppm: 0.87 (3H, t, J=7 Hz), 0.90–1.85 (11H, m), 1.90–2.05 (2H, m), 2.95–3.10 (2H, m), 3.15–3.30 (2H, m), 3.35–3.50 (1H, m), 3.65–3.90 (1H, m), 4.14 (2H, t, J=6 Hz), 5.49 (1H, d, J=4 Hz), 6.76 (1H, t, J=5 Hz), 7.40–7.60 (3H, m), 7.86 (1H, d, J=9 Hz), 8.31 (1H, d, J=9 Hz)

REFERENCE EXAMPLE 23

To a solution of 2-chloro-6-{3-[3-cyclohexyl-3-(2-hydroxybutyl)ureido]-propoxy}quinoline (6.3 g), 4-dimethylaminopyridine (0.1 g) and triethylamine (2.3 g) in methylene chloride (80 ml) is added dropwise with stirring acetic anhydride (1.8 g) at room temperature. The methylene chloride layer is washed successively with diluted hydrochloric acid, water and a saturated aqueous sodium hydrogen carbonate solution, and dried over anhydrous magnesium sulfate. The resultant is concentrated under reduced pressure to remove the solvent to give 2-chloro-6-[3-[3-cyclohexyl-3-(2-acetyloxybutyl)ureido]-propoxy]quinoline (6.7 g) as a colorless oil.

¹H-NMR (DMSO-d₆) δ ppm: 0.81 (3H, t, J=7 Hz), 0.90–1.80 (11H, m), 1.80–2.10 (5H, m), 3.00–3.45 (4H, m), 3.55–3.70 (1H, m), 4.13 (2H, t, J=6 Hz), 4.35–5.00 (1H, m), 6.34 (1H, t, J=5 Hz), 7.35–7.60 (3H, m), 7.86 (1H, d, J=9 Hz), 8.31 (1H,d,J=9 Hz)

REFERENCE EXAMPLE 24

To a solution of 2-chloro-6-{3-[3-cyclohexyl-3-(2-acetyloxybutyl)ureido]propoxy}quinoline (5.6 g) in dimethylformamide (80 ml) is added sodium hydride (60% oily, 0.8 g), and the mixture is stirred at room temperature for one hour. To the reaction solution is added methyl iodide (1.1 ml), and the mixture is stirred for one hour. To the mixture is further added methyl iodide (2 ml), and the mixture is stirred at room temperature overnight. The reaction solution is poured into water, and extracted with ethyl acetate. The ethyl acetate layer is separated, washed with water, and dried over anhydrous magnesium sulfate. The resultant is concentrated under reduced pressure to remove the solvent, and the residue is purified by silica gel column chromatography (solvent; methylene chloride:methanol=20:1) to give 2-chloro-6-{3-[1-methyl-3-cyclohexyl-3-(2-acetyloxybutyl)ureido]propoxy}quinoline (5.5 g) as a colorless oil.

$^1$H-NMR (DMSO-d$_6$) δ ppm: 0.79 (3H, t, J=7 Hz), 0.90–1.85 (11H, m), 1.90–2.15 (5H, m), 2.75 (3H, s), 2.80–2.95 (1H, m), 3.00–3.45 (5H, m), 4.10 (2H, t, J=6 Hz), 4.65–4.80 (1H, m), 7.35–7.50 (2H, m), 7.53 (1H, d, J=9 Hz), 7.87 (1H, d, J=10 Hz), 8.30 (1H, d, J=9 Hz)

REFERENCE EXAMPLE 25

(R,R)-(−)-6-{3-[3-(trans-2-Hydroxycyclohexyl)-3-cyclopropylureido]-propoxy}carbostyril (10 g) and N,N-diisopropylethylamine (5.66 g) are dissolved in anhydrous methylene chloride (200 ml), and thereto is added dropwise with stirring chloromethyl methyl ether (2.28 g) under ice-cooling. The mixture is stirred under ice-cooling for one hour, and the mixture is stirred at room temperature overnight. To the reaction solution is added a saturated aqueous sodium hydrogen carbonate solution, and the mixture is extracted with methylene chloride. The extract is washed successively with water and a saturated sodium chloride solution, and dried over anhydrous sodium sulfate. The resultant is concentrated under reduced pressure to remove the solvent, and the residue is purified by silica gel column chromatography (solvent; methylene chloride:methanol=50:1→30:1), and recrystallized from diethyl ether-petroleum ether to give (R,R)-(−)-6-{3-[3-(trans-2-hydroxycyclohexyl)-3-cyclopropylureido]propoxy}-2-methoxymethoxyquinoline (3.33 g) as a white powder.

$^1$H-NMR (CDCl$_3$) δ ppm: 0.67–1.02 (4H, m), 1.15–1.40 (3H, m), 1.63–1.95 (4H, m), 2.05–2.18 (3H, m), 2.35–2.48 (1H, m), 3.39-3.83 (8H, m, with 3.58 (s)), 4.14 (2H, t, J=6 Hz), 5.66 (2H, s), 5.71 (1H, t, J=5.5 Hz), 6.94 (1H, d, J=8.5 Hz), 7.06 (1H, d, J=2.5 Hz), 7.25 (1H, dd, J=2.5, 9 Hz), 7.75 (1H, d, J=9 Hz), 7.94 (1H, d, J=8.5 Hz)

REFERENCE EXAMPLE 26

(R,R)-(−)-6-{3-[3-(trans-2-Hydroxycyclohexyl)-3-cyclopropylureido]-propoxy}-2-methoxymethoxyquinoline (2.83 g) is dissolved in dimethylformamide (50 ml), and thereto is added sodium hydride (60% oily dispersion, 0.383 g) at room temperature under argon atmosphere, and the mixture is stirred at room temperature for one hour. To the mixture is added 1-bromo-3-(2-tetrahydropyranyloxy)propane (2.14 g), and the mixture is heated with stirring at 70–90° C. for 5 hours. To the reaction solution is added water, and the mixture is extracted with ethyl acetate. The extract is washed successively with water and a saturated aqueous sodium chloride solution, and dried over anhydrous sodium sulfate. The resultant is concentrated under reduced pressure to remove the solvent, and the residue is purified by silica gel column chromatography (solvent; ethyl acetate:n-hexane=1:1) to give (R,R)-(−)-6-{3-[3-(trans-2-[3-(2-tetrahydropyranyloxy)propoxy]cyclohexyl)-3-cyclopropylureido]propoxy}-2-methoxymethoxyquinoline (1.7 g) as a white powder.

$^1$H-NMR (CDCl$_3$) δ ppm: 0.60–0.95 (4H, m), 1.02–1.47 (2H, m), 1.48–1.95 (14H, m), 2.02–2.26 (5H, m), 2.49–2.63 (1H, m), 3.33–3.52 (6H, m), 3.58 (3H, s), 3.60–3.96 (4H, m), 4.12 (2H, t, J=5 Hz), 4.45–4.60 (1H, m), 5.52–5.60 (1H, m), 5.67 (2H, s), 6.93 (1H, d, J=9 Hz), 7.06 (1H, d, J=2.5 Hz), 7.20–7.45 (1H, m), 7.74 (1H, d, J=9 Hz), 7.94 (1H, d, J=9 Hz)

REFERENCE EXAMPLE 27

The corresponding staring compounds are treated in the same manner as in Reference Example 9 to give the following compounds.
(1) trans-N-(2-Hydroxycyclohexyl)-N-cycloheptylamine
 Colorless oil
 B.p. 140° C./3 mmHg
(2) trans-N-(2-Hydroxycyclohexyl)-N-cyclooctylamine
 White crystals
 B.p. 150° C./1 mmHg

REFERENCE EXAMPLE 28

N-Cyclohexyl-N-(2-hydroxybutyl)amine (3 g) is dissolved in tetrahydrofuran (50 ml), and thereto is added with stirring sodium hydride (60% oily dispersion, 2.1 g) under ice-cooling, and the mixture is heated with stirring at 60° C. for one hour. To the reaction mixture is added dropwise with stirring ethyl bromide (2.1 g) under ice-cooling, and the mixture is stirred at room temperature for 4 hours. Water is added to the reaction mixture, and the mixture is extracted with ethyl acetate. The extract is concentrated under reduced pressure to remove the solvent, and the residue is purified by silica gel column chromatography (solvent; methylene chloride:methanol:aqueous ammonia=100:10:1) to give N-cyclohexyl-N-(2-ethoxybutyl)amine(1.6 g) as a colorless oil.

$^1$H-NMR (CDCl$_3$) δ ppm: 0.90 (3H, t, J=7.5 Hz), 1.00–1.95 (11H, m), 2.35–2.45 (1H, m), 2.54–2.74 (2H, m), 3.30–3.40 (1H, m), 3.44–3.64 (2H, m)

REFERENCE EXAMPLE 29

To a solution of N-cyclohexyl-N-(2-hydroxybutyl)amine (49.2 g) in tetrahydrofuran (1 liter) is added with stirring sodium hydride (60% oily dispersion, 12.6 g) in portions at 0° C. The mixture is stirred at the same temperature for one hour, and thereto is added dropwise benzyl bromide (34 ml). The mixture is stirred at room temperature overnight, and the mixture is concentrated under reduced pressure to remove the solvent. To the residue is added water, and the mixture is extracted with chloroform. The extract is dried over anhydrous magnesium sulfate, concentrated under reduced pressure to remove the solvent, and the residue is purified by silica gel column chromatography (solvent; methylene chloride:methanol:aqueous ammonia=200:10:1) to give N-cyclohexyl-N-(2-benzyloxybutyl)amine (25.8 g) as a colorless oil.

$^1$H-NMR (CDCl$_3$) δ ppm: 0.94 (3H, t, J=7.5 Hz), 1.00–1.35 (5H, m), 1.50–1.95 (8H, m), 2.30–2.45 (1H, m), 2.60–2.80 (2H, m), 3.45–3.60 (1H, m), 4.50 (1H, d, J=11.5 Hz), 4.61 (1H, d, J=11.5 Hz), 7.25–7.40 (5H, m)

REFERENCE EXAMPLE 30

6-(3-Chloropropoxy)carbostyril (5 g) and 1-amino-2-propanol (24 ml) are dissolved in 2-propanol (100 ml), and the mixture is refluxed for 4 hours. After the reaction mixture is allowed to cool, the precipitated crystals are collected by filtration, washed with ethanol, and dried to give 6-[3-(2-hydroxypropyl)aminopropoxy]carbostyril (3.1 g) as a white powder.

$^1$H-NMR (DMSO-d$_6$) δ ppm: 1.03 (3H, d, J=6 Hz), 1.80–1.90 (2H, m), 2.40–2.43 (2H, m), 2.66 (2H, t, J=6.5 Hz), 3.60–3.70 (1H, m), 4.04 (2H, t, J=6.5 Hz), 4.40–4.50 (1H, m), 6.48 (1H, d, J=9.5 Hz), 7.11–7.25 (3H, m), 7.83 (1H, d, J=9.5 Hz)

REFERENCE EXAMPLE 31

A solution of 6-(3-chloropropoxy)carbostyril (5.0 g) and 3-amino-1-propanol (24 ml) in methanol (25 ml) is heated at 100° C. for 4 hours in an autoclave. The mixture is concentrated under reduced pressure to remove the solvent, and the residue is purified by silica gel column chromatography (solvent; methylene chloride:methanol:aqueous ammonia= 70:10:1), and recrystallized from methanol-diethyl ether to give 6-[3-(3-hydroxypropyl)aminopropoxy]carbostyril(4.4 g) as a white powder.

$^1$H-NMR (DMSO-$d_6$) δ ppm: 1.45–1.65 (2H, m), 1.80–1.95 (2H, m), 2.40–2.75 (4H, m), 3.46 (2H, t, J=6.5 Hz), 4.03 (2H, t, J=6.5 Hz), 6.48 (1H, d, J=9.5 Hz), 7.10–7.30 (3H, m), 7.83 (1H, d, J=9.5 Hz)

REFERENCE EXAMPLE 32

The corresponding starting compounds are treated in the same manner as in Reference Example 1 to give the following compounds.

(1) 6-(3-Phthalimidopropoxy)-8-fluoro-3,4-dihydrocarbostyril

Pale yellow powder $^1$H-NMR (DMSO-$d_6$) δ ppm: 2.03 (2H, quint, J=6 Hz), 2.36–2.48 (2H, m), 2.70–2.90 (2H, m), 3.75 (2H, t, J=6.5 Hz), 3.97 (2H, t, J=6 Hz), 6.47 (1H, br-s), 6.55 (1H, dd, J=2.5, 12 Hz), 7.74–7.96 (4H, m), 9.91 (1H, s)

(2) 6-(3-Phthalimidopropoxy)-8-methoxycarbostyril

Pale yellow powder $^1$H-NMR (DMSO-$d_6$) δ ppm: 2.02–2.15 (2H, m), 3.77 (3H, s), 3.79 (2H, t, J=6.5 Hz), 4.04 (2H, t, J=5.5 Hz), 6.48 (1H, s), 6.49 (1H, d, J=9.5 Hz), 6.69 (1H, d, J=2 Hz), 7.77 (1H, d, J=9.5 Hz), 7.85–7.86 (5H, m), 7.80–7.90 (5H, m)

REFERENCE EXAMPLE 33

The corresponding starting compounds are treated in the same manner as in Reference Example 3 to give the following compounds.

(1) 6-[3-(1-Imidazolyl)carbonylaminopropoxy]-8-fluoro-3,4-dihydrocarbostyril

White powder $^1$H-NMR (DMSO-$d_6$) δ ppm: 1.97 (2H, quint, J=6 Hz), 2.38–2.51 (2H, m), 2.82–2.96 (2H, m), 3.33–3.47 (2H, m), 4.01 (2H, t, J=6.5 Hz), 6.66 (1H, s), 6.71 (1H, dd, J=2.5, 12.5 Hz), 7.03 (1H, s), 7.66 (1H, s), 8.23 (1H, s), 8.57 (1H, t, J=5.5 Hz), 9.93 (1H, s)

(2) 6-[3-(1-Imidazolyl)carbonylaminopropoxy]-8-fluorocarbostyril

White powder $^1$H-NMR (DMSO-$d_6$) δ ppm: 2.02 (2H, quint, J=6 Hz), 3.35–3.50 (2H, m), 4.10 (2H, t, J=6 Hz), 6.57 (1H, d, J=9.5 Hz), 7.03 (1H, s), 7.05–7.23 (2H, m), 7.67 (1H, s), 7.85 (1H, dd, J=1.5, 10 Hz), 8.24 (1H, s), 8.59 (1H, t,J=5.5 Hz), 11.67 (1H, br-s)

(3) 6-[3-(1-Imidazolyl)carbonylaminopropoxy]-8-methoxycarbostyril

Pale yellow powder $^1$H-NMR (DMSO-$d_6$) δ ppm: 2.00–2.05 (2H, m), 3.44 (2H, t, J=6 Hz), 3.86 (3H, s), 4.08 (2H, t, J=6 Hz), 6.50 (1H, d, J=9.5 Hz), 6.74 (1H, d, J=2 Hz), 6.78 (1H, d, J=2 Hz), 7.03 (1H, s), 7.67 (1H, s), 7.79 (1H, d, J=9.5 Hz), 8.24 (1H, s), 8.55–8.65(1H, m)

(4) 6-[2-(1-Imidazolyl)carbonylaminoethoxy]carbostyril

White powder $^1$H-NMR (DMSO-$d_6$) δ ppm: 3.60–3.72 (2H, m), 4.17 (2H t, J=5.5 Hz), 6.49 (1H, d, J=9.5 Hz), 7.03 (1H, s), 7.15–7.30 (3H, m), 7.69 (1H, s), 7.82 (1H, d, J=9.5 Hz), 8.26 (1H, s), 8.70–8.85 (1H, m)

(5) 6-[4-(1-Imidazolyl)carbonylaminobutoxy]carbostyril

White powder $^1$H-NMR (DMSO-$d_6$) δ ppm: 1.62–1.90 (4H, m), 3.25–3.50 (2H, m), 4.03 (2H, t, J=6 Hz), 6.49 (1H, d, J=9.5 Hz), 7.03 (1H, s), 7.10–7.30 (3H, m), 7.67 (1H, s), 7.82 (1H, d, J=9.5 Hz), 8.24 (1H, s), 8.48–8.60(1H, m), 11.65 (1H, br-s)

REFERENCE EXAMPLE 34

The corresponding starting compounds are treated in the same manner as in Reference Example 4 to give the following compounds.

(1) 6-(3-Chloropropoxy)-8-fluoro-3,4-dihydrocarbostyril

White powder $^1$H-NMR (DMSO-$d_6$) δ ppm: 2.22 (2H, quint, J=6 Hz), 2.64 (2H, t, J=6 Hz), 2.97 (2H, t, J=6 Hz), 3.73 (2H, t, J=6 Hz), 4.06 (2H, t, J=6 Hz), 6.50–6.63 (2H, m), 7.67 (1H, br-s)

(2) 6-(3-Chloropropoxy)-8-fluorocarbostyril

Pale yellow powder $^1$H-NMR (DMSO-$d_6$) δ ppm: 2.18 (2H, quint, J=6 Hz), 3.80 (2H, t, J=6.5 Hz), 4.13 (2H, t, J=6 Hz), 6.57 (1H, d, J=10 Hz), 7.07–7.23 (2H, m), 7.87 (1H, dd, J=1.5, 10 Hz), 11.65 (1H, br-s)

(3) 6-(2-Bromoethoxy)carbostyril

White powder $^1$H-NMR (DMSO-$d_6$) δ ppm: 3.81 (2H, t, J=5.5 Hz), 4.34 (2H, t, J=5.5 Hz), 6.49 (1H, d, J=9.5 Hz), 7.14–7.30 (3H, m), 7.82 (1H, d, J=9.5 Hz), 11.61 (1H, br-s)

(4) 6-(4-Bromobutoxy)carbostyril

White powder $^1$H-NMR (DMSO-$d_6$) δ ppm: 1.75–2.10 (4H, m), 3.62 (2H, t, J=6.5 Hz), 4.02 (2H, t, J=6 Hz), 6.50 (1H, d, J=9.5 Hz), 7.10–7.35 (3H, m), 7.84 (1H, d, J=9.5 Hz), 11.66 (1H, br-s)

REFERENCE EXAMPLE 35

The corresponding starting compounds are treated in the same manner as in Reference Example 5 to give the following compounds.

(1) 6-(3-Phthalimidopropoxy)-8-fluorocarbostyril

Pale yellow powder $^1$H-NMR (DMSO-$d_6$) δ ppm: 2.08 (2H, quint, J=6 Hz), 3.78 (2H, t, J=6.5 Hz), 4.06 (2H, t, J=6 Hz), 6.55 (1H, d, J=9.5 Hz), 6.91 (1H, dd, J=2.5, 12 Hz), 6.98 (1H, br-s), 7.76–7.96 (4H, m), 11.60 (1H, br-s)

(2) 6-(2-Phthalimidoethoxy)carbostyril

White powder $^1$H-NMR (DMSO-$d_6$) δ ppm: 3.99 (2H, t, J=5.5 Hz), 4.25 (2H, t, J=5.5 Hz), 6.47 (1H, d, J=10 Hz), 7.10–7.30 (3H, m), 7.75–7.79 (5H, m)

(3) 6-(4-Phthalimidobutoxy)carbostyril

Pale yellow powder $^1$H-NMR (DMSO-$d_6$) δ ppm: 1.67–1.90 (4H, m), 3.55–3.76 (2H, m), 3.91–4.16 (2H, m), 6.48 (1H, d, J=9.5 Hz), 7.08–7.32 (3H, m), 7.76–7.95 (5H, m)

REFERENCE EXAMPLE 36

The corresponding starting compounds are treated in the same manner as in Reference Example 2 to give the following compounds.

(1) 6-(3-Aminopropoxy)-8-fluorocarbostyril hydrochloride

White powder $^1$H-NMR (DMSO-$d_6$) δ ppm: 2.06 (2H, quint, J=6 Hz), 2.87–3.10 (2H, m), 4.12 (2H, t, J=6 Hz), 6.57 (1H, d, J=9.5 Hz), 7.07–7.26 (2H, m), 8.88 (1H, br-d, J=10 Hz), 8.05–8.45 (3H, m), 11.40–11.88 (1H, m)

(2) 6-(3-Aminopropoxy)-8-methoxycarbostyril hydrochloride

Pale yellow powder $^1$H-NMR (DMSO-$d_6$) δ ppm: 2.04–2.10 (2H, m), 2.96 (2H, t, J=6.5 Hz), 4.10 (2H, t, J=6 Hz), 6.55 (1H, d, J=9.5 Hz), 6.81–6.84 (2H, m), 7.85 (1H, d, J=9.5 Hz), 8.10–8.35 (3H, m)

(3) 6-(2-Aminoethoxy)carbostyril

White powder $^1$H-NMR (DMSO-$d_6$) δ ppm: 2.88 (2H, t, J=5.5 Hz), 3.93 (2H, t, J=5.5 Hz), 6.48 (1H, d, J=9.5 Hz), 7.11–7.25 (3H, m), 7.83 (1H, d, J=9.5 Hz)

(4) 6-(4-Aminobutoxy)carbostyril

Pale yellow powder $^1$H-NMR (DMSO-$d_6$) δ ppm: 1.67–1.97 (4H, m), 2.83 (2H, t, J=6.5 Hz), 4.01 (2H, t, J=6 Hz), 6.50 (1H, d, J=9.5 Hz), 7.10–7.37 (3H, m), 7.84 (1H, d, J=9.5 Hz)

REFERENCE EXAMPLE 37

To a solution of N-methylcyclohexylamine (17 g) in a 6N aqueous hydrochloric acid solution (90 ml) is added dropwise an aqueous solution (60 ml) of sodium nitrite (20.7 g) at 60° C. The mixture is stirred at the same temperature for 2 hours, and diluted with methanol (300 ml). To the mixture are added an aqueous solution (100 ml) of sodium hydroxide (45 g) and formamidine sulfinic acid (39 g). The mixture is refluxed for 2 hours, and diluted with water (400 ml). The mixture is extracted three times with methylene chloride, and the extract is washed with a saturated aqueous sodium chloride solution, dried over anhydrous magnesium sulfate, and concentrated under reduced pressure to remove the solvent. The residue is distilled under reduced pressure to give 1-methyl-1-cyclohexylhydrazine (10 g) as a colorless oil.

B.p. 76–78° C./19 mmHg

The corresponding starting compounds are treated in the same manner as in Reference Example 37 to give the following compound.

1-Cyclopropyl-1-cyclohexylhydrazine

Pale yellow oil $^1$H-NMR (CDCl$_3$) δ ppm: 0.46–0.60 (4H, m), 1.01–1.43 (5H, m), 1.56–1.70 (11H, m), 1.73–1.85 (2H, m), 1.81–2.08 (3H, m), 2.43–2.58 (11H, m), 3.06 (2H, br-s)

REFERENCE EXAMPLE 38

To a solution of N-(trans-2-hydroxycyclohexyl)-N-cyclopropylamine (20 g) in methyl ethyl ketone (260 ml) is added with stirring a solution of D-di-p-toluoyltartaric acid (49.8 g) in methyl ethyl ketone (200 ml) at room temperature. The mixture is stirred at room temperature for 1.5 hour, and the precipitated crystals are collected by filtration, and washed successively with methyl ethyl ketone and acetone. The crystals thus obtained are recrystallized from methanol-acetonitrile to give (R,R)-(-)-trans-N-(2-hydroxycyclohexyl)-N-cyclopropylamine D-di-p-toluoyltartrate (22.0 g) as a white powder.

M.p. 165° C.

REFERENCE EXAMPLE 39

To an aqueous solution (80 ml) of sodium hydroxide (4 g) is added with stirring (R,R)-(-)-trans-N-(2-hydroxycyclohexyl)-N-cyclopropylamine D-di-p-toluoyltartrate (20 g) at room temperature. The mixture is further stirred at room temperature for 0.5 hour, and extracted twice with ethyl acetate (40 ml). To the aqueous layer is added water (40 ml), and the mixture is further extracted three times with methylene chloride (20 ml). The organic layers are combined, and dried over anhydrous magnesium sulfate. The resultant is concentrated under reduced pressure to remove the solvent to give (R,R)-(-)-trans-N-(2-hydroxycyclohexyl)-N-cyclopropylamine (5.2 g) as colorless rods.

M.p. 43–45° C.

$[\alpha]_D^{24}$=−59.3 (c=1.0, methanol)

REFERENCE EXAMPLE 40

To a mixture of water (50 ml) and acetonitrile (50 ml) are added 6-(3-aminopropoxy)carbostyril hydrochloride (5.0 g) and potassium carbonate (3.4 g) at room temperature. The mixture is stirred at room temperature for 2 hours, and cooled to −5° C. To the mixture is added dropwise phenyl chlorocarbonate (3.9 g) while the temperature of the mixture is kept below 0° C. The mixture is stirred at the same temperature for 1 hour, and thereto is added water (100 ml), and then the mixture is further stirred for 0.5 hour. The precipitated crystals are collected by filtration, and washed successively with water and acetone to give 6-(3-phenoxycarbonylaminopropoxy)carbostyril (6.0 g) as a white powder.

$^1$H-NMR (DMSO-$d_6$) δ ppm: 1.95 (2H, quint, J=6.5 Hz), 3.20–3.35 (2H, m), 4.06 (2H, t, J=6.0 Hz), 6.50 (1H, d, J=9.5 Hz), 7.05–7.40 (8H, m), 7.75–7.95 (2H, m), 11.65 (1H, br-s)

EXAMPLE 1

6-[3-(1-Imidazolyl)carbonylaminopropoxy]carbostyfil (100 g) and trans-N-(2-hydroxycyclohexyl)-N-cyclopropylamine (49.6 g) are suspended in chloroform (1 liter), an the mixture is refluxed for 10 hours. The insoluble materials are removed by filtration on celite, and the filtrate is washed successively with water and a saturated aqueous sodium chloride solution, dried over anhydrous sodium sulfate, and concentrated under reduced pressure to remove the solvent. The residue is purified by silica gel column chromato-graphy (solvent; methylene chloride:ethyl acetate:methanol=10:10:1), and recrystallized from ethanol to give 6-{3-[3-(trans-2-hydroxycyclohexyl)-3-cyclopropylureido]propoxy}carbostyril (83 g) as a white powder.

M.p. 163.5–164.5° C.

Using the corresponding starting compounds, the compounds of Examples 7–31 are obtained in the same manner as in Example 1.

EXAMPLE 2

To a solution of 6-{3-[N-(trans-2-hydroxycyclohexyl)-N-cyclopropylamino]carbonylaminopropoxy}carbostyril (5 g), triethylamine (4.2 ml) and 4-dimethylaminopyridine (0.48 g) in methylene chloride (100 ml) is added dropwise with stirring acetic anhydride (3.17 ml) at room temperature. The mixture is stirred at room temperature for 2 hours, and thereto is added a 25% aqueous ammonia (20 ml), an the mixture is stirred for 1 hour. The organic layer is separated, washed successively with water and a saturated aqueous sodium chloride solution, dried over anhydrous sodium sulfate, and concentrated under reduced pressure to remove the solvent. The residue is purified by silica gel column chromatography (solvent; methylene chloride:methanol=20:1), and recrystallized from ethanol-diethyl ether to give 6-{3-[3-(trans-2-acetyloxycyclohexyl)-3-cyclopropylureide]propoxy}carbostyril (4.28 g) as a white powder.

M.p. 180–183° C.

Using the corresponding starting compounds, the compounds of Examples 11 and 14 are obtained in the same manner as in Example 2.

EXAMPLE 3

6-(3-Methylaminopropoxy)carbostyril (3 g) is dissolved in dimethylformamide (150 ml), and thereto are added N-methyl-N-cyclohexylaminocarbonyl chloride (2.3 g) and potassium carbonate (2 g). The mixture is stirred at room temperature overnight, and further heated with stirring at 80° C. for 2 hours. The reaction solution is poured into water, and extracted with ethyl acetate. The extract is concentrated under reduced pressure to remove the solvent, and the residue is purified by silica gel column chromatography (solvent; methylene chloride:methanol=30:1), and recrystallized from ethyl acetate to give 6-[3-(1,3-dimethyl-3-cyclohexylureido)propoxy]carbostyril (2.3 g) as a white powder.

M.p. 113–114° C.

EXAMPLE 4

To acetic acid (100 ml) is added 2-chloro-6-{3-[1-methyl-3-cyclohexyl-3-(2-acetyloxybutyl)ureido]propoxy}quinoline (5.5 g), and the mixture is refluxed for 4 hours. The mixture is concentrated under reduced pressure to remove the acetic acid, and the residue is dissolved in methylene chloride and washed with a saturated aqueous sodium hydrogen carbonate solution. The mixture is dried over anhydrous magnesium sulfate, and concentrated under reduced pressure to remove the solvent. The residue is purified by silica gel column chromatography (solvent; methylene chloride:methanol=20:1), and recrystallized from methylene chloride-diethyl ether to give 6-{3-[1-methyl-3-cyclohexyl-3-(2-acetyloxybutyl)ureido]propoxy}carbostyril (2.7 g) as a white powder.

M.p. 164–166° C.

EXAMPLE 5

6-{3-[1-Methyl-3-cyclohexyl-3-(2-acetyloxybutyl)ureido]propoxy}-carbostyril (1.63 g) is added to methanol (10 ml), and thereto is added dropwise a 10% aqueous potassium hydroxide solution (10 ml). The mixture is stirred at room temperature overnight, and concentrated under reduced pressure to remove the solvent. The resultant is poured into water, and extracted with chloroform. The extract is concentrated under reduced pressure to remove the solvent, and the residue is purified by silica gel column chromatography (solvent; methylene chloride:methanol=20:1), and recrystallized from methylene chloride-diethyl ether to give 6-{3-[1-methyl-3-cyclohexyl-3-(2-hydroxybutyl)ureido]propoxy}carbostyril (0.6 g) as a white powder.

M.p. 173–175° C.

Using the corresponding starting compounds, the compounds of Examples 6 and 8-10 disclosed hereinafter are obtained in the same manner as in Example 5.

EXAMPLES 6 TO 31

Using the corresponding starting compounds, the compounds as listed in Table 1 are obtained in the same manner as in Example 3 or 4.

TABLE 1

[Structure: carbostyril with O—A—N(R³)CON(R¹)(R²) substituent at 6-position and R at 7/8-position]

Example 6

A: —(CH$_2$)$_3$—   R: H

R$^1$: cyclopropyl

R$^2$: cyclohexyl with HO substituent   R$^3$: H

Racemic compound
Bond between 3- and 4-positions of the carbostyril nucleus: Double   M.p. 163.5–164.5° C.
Crystalline form: White powder   Form: Free   Solvent for recrystallization: Ethanol

Example 7

A: —(CH$_2$)$_3$—   R: H

R$^1$: cyclopropyl

R$^2$: cyclohexyl with H$_3$COCO substituent   R$^3$: H

TABLE 1-continued

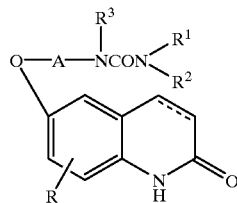

Racemic compound
Bond between 3- and 4-positions of the carbostyril nucleus: Double  M.p. 180–183° C.
Crystalline form: White powder    Form: Free    Solvent for recrystallization:
Ethanol-diethyl ether
Example 8

A: —(CH$_2$)$_3$—    R: H

R$^1$: 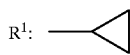    R$^2$: 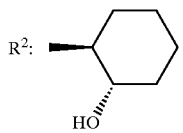    R$^3$: H (S,S)-(+)-isomer
Bond between 3- and 4-positions of the carbostyril nucleus: Double  M.p. 157–159° C.
Crystalline form: White powder    Form: Free    Solvent for recrystallization: Ethanol
[α]$_D^{24}$ = +1.4° (c = 1.0, methanol)
Example 9

A: —(CH$_2$)$_3$—    R: H

R$^1$: 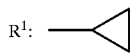    R$^2$: 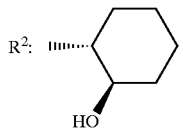    R$^3$: H (R,R)-(−)-isomer
Bond between 3- and 4-positions of the carbostyril nucleus: Double  M.p. 158.5–160° C.
Crystalline form: White powder    Form: Free    Solvent for recrystallization: Ethanol
[α]$_D^{24}$ = −1.3° (c = 1.0, methanol)
Example 10

A: —(CH$_2$)$_3$—    R: H

R$^1$: 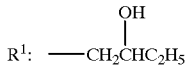    R$^2$: 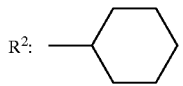    R$^3$: H

Bond between 3- and 4-positions of the carbostyril nucleus: Double  M.p.
104–111° C.    Crystalline form: White powder    Form: Free
Solvent for recrystallization: Ethanol-water
Example 11

A: —(CH$_2$)$_3$—    R: H

R$^1$: 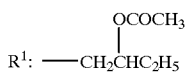    R$^2$: 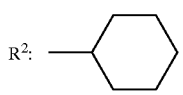    R$^3$: H

Bond between 3- and 4-positions of the carbostyril nucleus: Double  M.p. 165–167° C.
Crystalline form: White powder    Form: Free    Solvent for recrystallization: Ethanol
Example 12

A: —(CH$_2$)$_3$—    R: H

R$^1$: —CH$_3$    R$^2$: 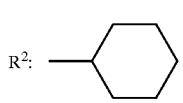    R$^3$: —CH$_3$

TABLE 1-continued

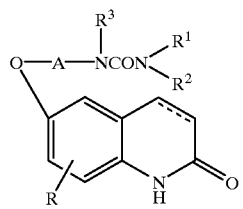

Bond between 3- and 4-positions of the carbostyril nucleus: Double M.p. 113–114° C.
Crystalline form: White powder    Form: Free    Solvent for recrystallization: Ethyl acetate
Example 13

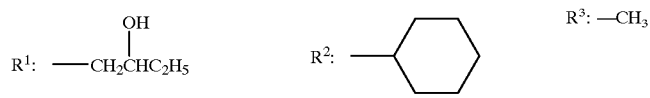

Bond between 3- and 4-positions of the carbostyril nucleus: Double M.p. 173–175° C.
Crystalline form: White powder    Form: Free    Solvent for recrystallization: Methylene chloride-diethyl ether
Example 14

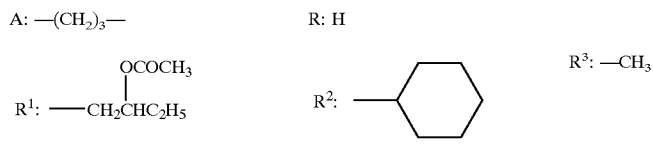

Bond between 3- and 4-positions of the carbostyril nucleus: Double M.p. 164–166° C.
Crystalline form: White powder    Form: Free    Solvent for recrystallization: Methylene chloride-diethyl ether
Example 15

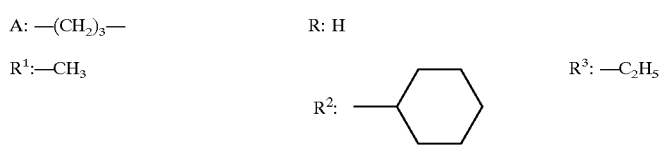

Bond between 3- and 4-positions of the carbostyril nucleus: Double M.p. 136–137° C.
Form: Free
Example 16

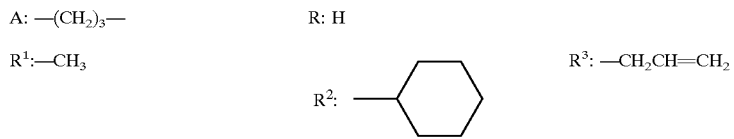

Bond between 3- and 4-positions of the carbostyril nucleus: Double M.p. 116–117° C.
    Form: Free
Example 17

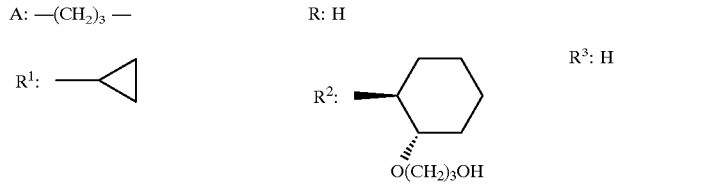

(R,R)-(−)-isomer
Bond between 3- and 4-positions of the carbostyril nucleus: Double M.p. 105–108° C.
Crystalline form: White powder    Form: Free    Solvent for recrystallization: Dichloromethane-diethyl ether
$[\alpha]_D^{21} = -21.9°$ (c = 1.00, methanol)

TABLE 1-continued

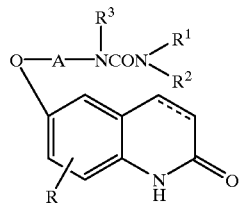

Example 18

A: —(CH$_2$)$_3$—    R: H

R$^1$: 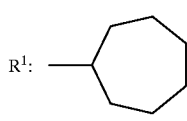    R$^2$: 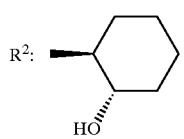    R$^3$: H

Racemic compound
Bond between 3- and 4-positions of the carbostyril nucleus: Double M.p. 105–106° C.
Crystalline form: White powder    Form: Free    Solvent for recrystallization: Ethanol Example 19

A: —(CH$_2$)$_3$—    R: H

R$^1$: —CH$_2$CHC$_2$H$_5$
            |
            OC$_2$H$_5$

R$^2$: 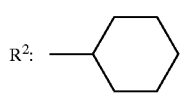    R$^3$: H

Bond between 3- and 4-positions of the carbostyril nucleus: Double M.p. 122–125° C.
Crystalline form: White powder    Form: Free    Solvent for recrystallization:
Ethanol-diethyl ether Example 20

A: —(CH$_2$)$_3$—    R: H

R$^1$: —CH$_2$CHC$_2$H$_5$
            |
            OCH$_2$— 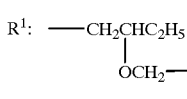

R$^2$: 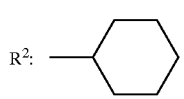    R$^3$: H

Bond between 3- and 4-positions of the carbostyril nucleus: Double M.p. 121–123° C.
Crystalline form: White powder    Form: Free    Solvent for recrystallization: n-Hexane Example 21

A: —(CH$_2$)$_3$—    R: H

R$^1$: —CH$_3$    R$^2$: 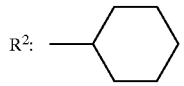    R$^3$: —CH$_2$CHCH$_3$
                                                            |
                                                            OH Bond between 3- and 4-positions of the carbostyril nucleus: Double M.p. 127–129° C.
Crystalline form: White powder    Form: Free    Solvent for recrystallization:
Di-chloromethane-ethyl acetate methanol Example 22

A: —(CH$_2$)$_3$—    R: H

R$^1$: —CH$_3$    R$^2$: 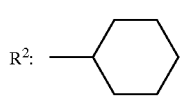    R$^3$: —(CH$_2$)$_3$OH

Bond between 3- and 4-positions of the carbostyril nucleus: Double M.p. 141–142° C.
Crystalline form: White powder    Form: Free    Solvent for recrystallization: Ethanol TABLE 1-continued

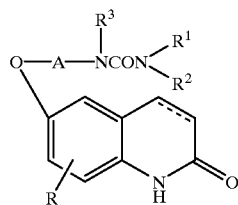

Example 23

A: —(CH$_2$)$_3$—  R: H

R$^1$: —CH$_3$  R$^2$: 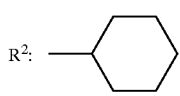  R$^3$: —CH$_2$CH$_2$CH$_3$

Bond between 3- and 4-positions of the carbostyril nucleus: Double  M.p. 119–119.5° C.
Crystalline form: Colorless flakes  Form: Free  Solvent for recrystallization:
Ethanol-diethyl ether Example 24

A: —(CH$_2$)$_3$—  R: H

R$^1$: 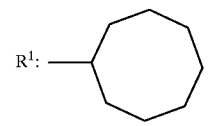  R$^2$: 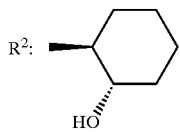  R$^3$: H

Racemic compound

Bond between 3- and 4-positions of the carbostyril nucleus: Double  M.p. 110–114° C.
Crystalline form: White powder  Form: Free  Solvent for recrystallization: Ethanol Example 25

A: —(CH$_2$)$_3$—  R: 8-F

R$^1$:   R$^2$: 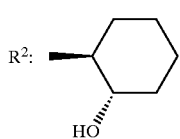  R$^3$: H

Racemic compound

Bond between 3- and 4-positions of the carbostyril nucleus: Single  M.p. 142–143° C.
Crystalline form: White powder  Form: Free  Solvent for recrystallization: Di-
chloromethane-diethyl ether Example 26

A: —(CH$_2$)$_3$—  R: 8-F

R$^1$: 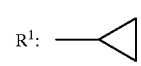  R$^2$: 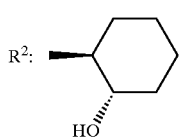  R$^3$: H

Racemic compound

Bond between 3- and 4-positions of the carbostyril nucleus: Double  M.p. 186–189° C.
Crystalline form: White powder  Form: Free  Solvent for recrystallization: Ethanol TABLE 1-continued

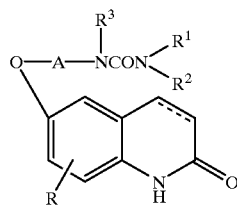

Example 27

A: —(CH₂)₃—          R: 8-OCH₃

R¹: 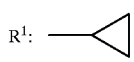          R²: 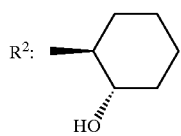          R³: H

Racemic compound

Bond between 3- and 4-positions of the carbostyril nucleus: Double  M.p. 161–162° C.
Crystalline form: White powder    Form: Free    Solvent for recrystallization: Ethanol Example 28

A: —(CH₂)₃—          R: H

R¹: H          R²: 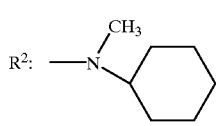          R³: H

Bond between 3- and 4-positions of the carbostyril nucleus: Double  M.p. 169–171° C.
Crystalline form: White powder    Form: Free    Solvent for recrystallization:
Ethanol-diethyl ether Example 29

A: —(CH₂)₃—          R: H

R¹: H          R²: 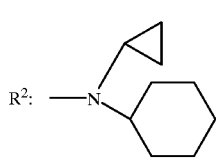          R³: H

Bond between 3- and 4-positions of the carbostyril nucleus: Double  M.p. 187–188.5° C.
Crystalline form: White powder    Form: Free    Solvent for recrystallization: Ethanol Example 30

A: —(CH₂)₂—          R: H

R¹:           R²: 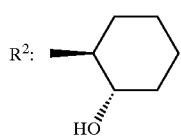          R³: H

Racemic compound

Bond between 3- and 4-positions of the carbostyril nucleus: Double  M.p. 163–165° C.
Crystalline form: White powder    Form: Free    Solvent for recrystallization: Ethanol TABLE 1-continued

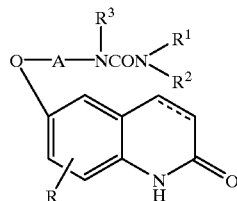

Example 31

A: —(CH$_2$)$_4$—  R: H

R$^1$: 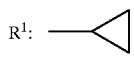   R$^2$: 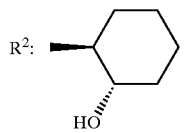   R$^3$: H (R,R)-(−)-isomer

Bond between 3- and 4-positions of the carbostyril nucleus: Double M.p. 94–97° C.
Crystalline form: White powder    Form: Free    Solvent for recrystallization: Ethanol
$[\alpha]_D^3 = -1.0°$ (c = 1.0, methanol)

EXAMPLE 32

(R,R)-(−)-6-{3-[3-[trans-2-[3-(2-Tetrahydropyranyloxy)propoxy]cyclohexyl]-3-cyclopropylureido]propoxy}-2-methoxymethoxyquinoline (1.7 g) is dissolved in ethanol (17 ml), and thereto is added dropwise with stirring a 2N hydrochloric acid (17 ml) at room temperature. The mixture is stirred at room temperature for 2 hours, and concentrated under reduced pressure to remove the ethanol. The residue is purified by silica gel column chromatography (solvent; ethyl acetate:n-hexane=1:1), and recrystallized from methylene chloride-diethyl ether to give (R,R)-(−)-6-{3-[3-[trans-2-(3-hydroxypropoxy)cyclohexyl]-3-cyclopropylureido]propoxy}carbostyril (1.2 g) as a white powder.

M.p. 105–108° C.

$[\alpha]_D^{21} = -21.9°$ (c=1.00, methanol)

EXAMPLE 33

6-[3-(3-Cyclohexyl-3-methyl-1-allylureido)propoxy]carbostyril (3.0 g) is dissolved in ethanol (90 ml), and thereto is added 10% palladium-carbon (0.3 g), and the mixture is subjected to catalytic hydrogenation under 1 atm of hydrogen gas at room temperature. After the reaction is complete, the catalyst is removed by filtration, and the filtrate is concentrated under reduced pressure. The residue is purified by silica gel column chromatography (solvent; methylene chloride:methanol=20:1), and recrystallized from ethanol-diethyl ether to give 6-[3-(3-cyclohexyl-3-methyl-1-propylureido)propoxy]carbostyril (2.1 g) as colorless flakes.

M.p. 119–119.5° C.

The corresponding starting compounds are treated in the same manner as in Example 33 to give the compound of Example 15.

EXAMPLE 34

To a mixture of dimethylformamide (45 ml) and water (5 ml) are added 6-(3-phenoxycarbonylaminopropoxy)carbostyril (5.0 g) and (R,R)-(−)-N-(trans-2-hydroxycyclohexyl)-N-cyclopropylamine (2.4 g), and the mixture is heated with stirring at 85° C. for 6 hours. To the mixture is added water (80 ml) at 80° C., and the mixture is allowed to cool while the mixture is stirred overnight. The precipitated crystals are collected by filtration, washed with water, and purified by silica gel column chromatography (solvent; methylene chloride:methanol: ethyl acetate=5:1:5), and recrystallized from ethanol to give (R,R)-(−)-6-{3-[3-(trans-2-hydroxycyclohexyl)-3-cyclopropylureido]propoxy}carbostyril (2.9 g) as a white powder.

M.p. 158.5–160° C.

$[\alpha]_D^{24} = -1.30$ (c=1.0, methanol)

The corresponding starting compounds are treated in the same manner as in Example 34 to give the compounds of Examples 6–8 and 10–31.

Pharmacological Experiment 1 Platelet aggregation inhibitory activity (1) Preparation of platelet rich plasma (PRP):

The blood was collected from the carotid of a male rabbit without anesthesia (NZW species, body weight; 2–3 kg) with mixing thereof with $\frac{1}{10}$ volume of citric acid. The blood thus obtained was separated and put into plastic test tubes (each about 7 ml), and centrifuged at 900 rpm for 15 minutes at room temperature to give a turbid supernatant as a platelet rich plasma (PRP). The residue from which PRP is separated was centrifuged at 3000 rpm for 10 minutes, and the supernatant was collected as a platelet poor plasma (PPP). The PRP was diluted with PPP so that the concentration thereof was adjusted to $5 \times 10^5$ cells/i, and used in the platelet aggregation inhibitory activity test.

(2) Method for platelet aggregation inhibitory activity test:

The platelet aggregation was tested according to Born's turbidimetry. That is, a test compound was dissolved in dimethylformamide, and the test compound solution (1 μl) thus obtained was put into a cuvette, and thereto was further added PRP (200 μl). Immediately thereafter, the cuvette was set into an apparatus for determining platelet aggregation activity, PAM-8T (manufactured by Mevanix Inc.), and the mixture was incubated at 37° C. Precisely three minutes thereafter, a solution of adenosine diphosphate (ADP, PA test ADP [MCM], purchased by MC Medical Ltd.) in physiological saline solution or a collagen solution (Collagenreagent Horm, purchased by MC Medical Ltd.) (20 μl) was added thereto. The final concentration of the ADP solution or the collagen solution was 7.5 μM or 20 μg/ml, respectively.

The maximum aggregation rate and the aggregation inhibitory rate were calculated by the following equations.

$$\text{Maximum AggregationRate} = \frac{X - \text{Optical transmission of } PRP}{\text{Optical transmission of } PPP - \text{Optical transmission of } PRP} \times 100$$

$X$: Maximum optical transmission on the aggregation response curve $$\text{Aggregation Inhibitory Rate} = \left(1 - \frac{\text{Maximum Aggregation Rate of } PRP \text{ treated by a test compound}}{\text{Maximum Aggregation Rate of } PRP \text{ treated by a solvent}}\right) \times 100$$

$IC_{50}$, which is a concentration of the test compound being required to inhibit the platelet aggregation reaction by 50%, was determined from the aggregation inhibitory rates at two different concentrations of a test compound. The results are shown in Table 2.

TABLE 2

| Test Compound No. | ADP $IC_{50}$ (μmole) | Collagen $IC_{50}$ (μmole) |
| --- | --- | --- |
| The compound of Ex. 6 | 1.8 | 1.9 |
| The compound of Ex. 7 | 18.2 | 2.1 |
| The compound of Ex. 8 | 2.1 | 2.0 |
| The compound of Ex. 9 | 1.9 | 2.0 |
| The compound of Ex. 10 | 0.4 | 0.3 |
| The compound of Ex. 11 | 0.6 | 2.1 |
| The compound of Ex. 12 | 31.6 | 20.5 |
| The compound of Ex. 13 | 2.1 | 2.0 |
| The compound of Ex. 14 | 1.5 | 2.2 |
| The compound of Ex. 15 | 15.2 | 16.1 |
| The compound of Ex. 16 | 4.6 | 20.0 |
| The compound of Ex. 17 | 0.14 | 2.39 |
| The compound of Ex. 18 | 0.12 | 0.03 |
| The compound of Ex. 19 | 0.18 | 0.59 |
| The compound of Ex. 20 | 0.22 | 0.29 |
| The compound of Ex. 21 | 2.08 | 3.25 |
| The compound of Ex. 22 | 1.31 | 2.80 |
| The compound of Ex. 23 | 13.4 | 2.51 |
| The compound of Ex. 24 | 0.08 | 0.03 |
| The compound of Ex. 25 | 4.65 | 3.90 |
| The compound of Ex. 26 | 0.45 | 3.03 |
| The compound of Ex. 27 | 31.6 | 31.6 |
| The compound of Ex. 28 | 0.11 | 0.10 |
| The compound of Ex. 29 | 0.01 | 0.03 |
| The compound of Ex. 30 | 3.67 | 2.94 |
| The compound of Ex. 31 | 15.7 | 2.57 |

Pharmacological Experiment 2 Antithrombotic activity

Antithrombotic activity of the test compounds was estimated by an inhibitory activity of the test compound by oral administration against death induced by pulmonary infarction in mice which was introduced by intravenous administration of collagen (pulmonary infarction inhibitory activity).

Male ICR mice (5-week old, body weight; about 25 g) was fasted overnight, and separated into groups (15 mice per each group) and numbered. A test compound solution, which was prepared by suspending a test compound in 1% hydroxypropylmethyl cellulose 2910 TC-5 (HPMC, manufactured by Shin-etsu Chemical Co., Ltd.), was orally administered to the mice, and 10 minutes thereafter, a collagen solution (the method for preparation thereof and a dose thereof are explained hereafter) was injected to the mice at the tail vein at the constant rate. The lethality of the mice was determined by the number of mice which were died in an hour after the administration of collagen solution. The antithrombotic activity of the test compound was estimated by the inhibitory rate (%) of the lethality of the mice. The collagen solution was prepared by dissolving collagen (Type III, manufactured by Sigma Chemical Ltd.) in 0.05 M acetic acid solution containing 2 mM calcium chloride and 5% glucose at 4° C. so that the final concentration of collagen was adjusted to 2.5 mg/ml, and then the pH value thereof was adjusted to pH 7.4 with sodium hydroxide the day before the experiment. The collagen solution was incubated with stirring at 37° C. for two hours, and then further stirred at room temperature overnight. Just before the experiment, the pH value of the collagen solution was adjusted again to pH 7.4. The amount of the collagen solution which was injected at the tail vein was previously determined so that the lethality by pulmonary infarction induced thereby became about 75%. The results are shown in Table 3.

TABLE 3

| Test Compound No. | Pulmonary infarction inhibitory activity (%) 30 mg/kg |
| --- | --- |
| The compound of Ex. 6 | 100 |
| The compound of Ex. 7 | 67 |
| The compound of Ex. 8 | 100 |
| The compound of Ex. 9 | 100 |
| The compound of Ex. 10 | 74 |
| The compound of Ex. 11 | 80 |
| The compound of Ex. 12 | 100 |
| The compound of Ex. 13 | 58 |
| The compound of Ex. 14 | 66 |
| The compound of Ex. 15 | 86 |
| The compound of Ex. 16 | 77 |
| The compound of Ex. 17 | 100 |
| The compound of Ex. 18 | 69 |
| The compound of Ex. 19 | 84 |
| The compound of Ex. 20 | 66 |
| The compound of Ex. 21 | 59 |
| The compound of Ex. 22 | 69 |
| The compound of Ex. 23 | 90 |
| The compound of Ex. 24 | 100 |
| The compound of Ex. 25 | 100 |
| The compound of Ex. 26 | 85 |
| The compound of Ex. 27 | 80 |
| The compound of Ex. 28 | 100 |
| The compound of Ex. 29 | 91 |
| The compound of Ex. 30 | 100 |
| The compound of Ex. 31 | 48 |

Pharmacological Experiment 3 Intima thickening inhibitory activity

Male SD rats (6-week old) were separated into groups (8 rats per each group) and numbered. A test compound solution, which was prepared by suspending a test compound in 1% hydroxypropylmethyl cellulose 2910 TC-5 (HPMC, manufactured by Shin-etsu Chemical Co., Ltd.) was orally administered to the rats. In the control group, 1% HPMC solution was orally administered instead of the test compound solution. One or two hours thereafter, two french balloon catheters (manufactured by Baxter Travenol Inc.) were inserted into the left common carotid artery of the rats, and the artery was injured by abrading five times with a balloon. The day of balloon abrasion was considered as Day 0. On the following day (Day 1), a test compound was orally administered to the rats two times a day (in the morning and in the evening). On Day 2, 1.48 MBq/ml of $^3$H-thymidine (dose: 5 ml/kg, manufactured by NEN Research Products, Ltd.) was injected at the tail vein of the rats about one hour after the administration of the test compound so that the time after the balloon injury was fixed to the same in each rat. Precisely 45 minutes after the injection of $^3$H-thymidine at the tail veil, the common carotid artery of the rats was taken out.

In the test compound-treated group, only the left common carotid artery which was injured by balloon was taken out, and in the control group, both the left and right common carotid arteries were taken out. The common carotid artery thus obtained was cut to pieces of exact 1 cm long, and the unnecessary portions such as the outer membrane or the nerves were completely removed. The common carotid artery was put into a glass vial, and thereto was added a 0.5 N sodium hydroxide (0.5 ml), and the mixture was incubated at 37° C. overnight to be solubilized. The mixture was neutralized with a 5 N hydrochloric acid (0.05 ml), and thereto was further added an aqueous hydrogen peroxide solution (0.1 ml). Aquasol II (10 ml, manufactured by Du Pont Co.) was added thereto, and the mixture was well stirred and then allowed to stand for 30 minutes. The radioactivity of tritium in the mixture was counted by liquid scintillation counter. The intima thickening inhibitory activity of the test compound was calculated by the following equation.

$$\text{Intima Thickening Inhibitory Rate } (\%) = \frac{L(c) - L}{L(c) - R(c)} \times 100$$

L (c): The amount of tritium in the left common carotid artery in the control group (dpm)
R (c): The amount of tritium in the right common carotid artery in the control group (dpm)
L: The amount of tritium in the left common carotid artery in the test compound-treated group (dpm)

The results are shown in Table 4.

TABLE 4

| Test Compound No. | Dose (mg/kg) | Intima thickening inhibitory activity (%) |
|---|---|---|
| The compound of Ex. 6 | 10 | 31.4 |
| The compound of Ex. 7 | 30 | 15.2 |
| The compound of Ex. 8 | 30 | 13.3 |
| The compound of Ex. 9 | 10 | 26.8 |
| The compound of Ex. 10 | 30 | 34.2 |
| The compound of Ex. 11 | 30 | 33.0 |
| The compound of Ex. 12 | 30 | 21.1 |
| The compound of Ex. 13 | 30 | 16.6 |
| The compound of Ex. 14 | 30 | 15.7 |
| The compound of Ex. 15 | 30 | 11.9 |
| The compound of Ex. 16 | 30 | 33.3 |
| The compound of Ex. 17 | 30 | 16.0 |
| The compound of Ex. 18 | 30 | 19.0 |
| The compound of Ex. 19 | 30 | 23.4 |
| The compound of Ex. 26 | 30 | 16.0 |
| The compound of Ex. 28 | 30 | 27.8 |
| The compound of Ex. 29 | 30 | 29.3 |

Pharmacological Experiment 4
cGMP-inhibited cAMP phosphodiesterase (PDE3) inhibitory activity The PDE3 inhibitory activity of the present compounds was determined according to the method disclosed in Biochemica et Biophysica Acta, 429, pp. 485–497 (1976) and Biochemical Medicine, 10, pp. 301–311 (1974).

A PDE enzyme was a recombinant enzyme which was prepared by expressing in insect cell Sf9 by baculovirus expression system from cDNA of PDE3 (cf. Diabetes, 44, p. 67, (1995)). The cDNA was human myocardial cyclic-GMP inhibited PDE (hcGIP2, reference; Proc. Natl. Acad. Sci. USA, 89, 3721, (1992), GenBank M91667).

The PDE activity was tested in a reaction mixture (200 $\mu$l) of 50 mM Tris-HCl buffer (pH 8.0), 0.5 mM MgCl$_2$, 2 mM EGTA, 0.1 mg/ml BSA, 0.4 $\mu$M [8-$^3$H]cAMP, a PDE enzyme and a test compound. The reaction mixture was incubated at 30° C. for 15 minutes to make the PDE enzyme work, and then the reaction was quenched by incubating at 100° C. for 6 minutes in order to inactivate the PDE enzyme. The reaction mixture was cooled, and added thereto snake venom so that the final concentration thereof was 0.1 mg/ml. The mixture was incubated at 30° C. for 10 minutes to generate [8-$^3$H] adenosine. The [8-3H] adenosine thus obtained was isolated and collected by cation ion exchange column and the radioactivity thereof was determined by liquid scintillation counter.

The test compounds were dissolved in N,N-dimethylformamide (DMF), and the test compound solution thus obtained was added to the reaction mixture so that the final concentration thereof in the reaction mixture was controlled to 0.5%. Each assay was done in duplicate. The PDE activity (Vs) in the reaction mixture at each concentration of the test compound was estimated from the test results, and the PDE activity inhibitory activity (%) of the test compound was calculated according to the following equation based on the PDE activity (Vc) in the control group wherein DMF was used instead of the test compound solution.

$$\text{PDE Activity Inhibitory Rate } (\%) = \frac{Vc - Vs}{Vc} \times 100$$

The PDE inhibitory activity was expressed by IC$_{50}$, which is a concentration of the test compound being required to inhibit the PDE activity by 50%. The results are shown in Table 5.

TABLE 5

| Test Compound No. | PDE inhibitory activity IC$_{50}$ (mole) |
|---|---|
| The compound of Ex. 8 | $1.13 \times 10^{-7}$ |
| The compound of Ex. 9 | $9.30 \times 10^{-8}$ |
| The compound of Ex. 10 | $2.43 \times 10^{-8}$ |
| The compound of Ex. 12 | $1.97 \times 10^{-7}$ |
| The compound of Ex. 17 | $6.08 \times 10^{-8}$ |
| The compound of Ex. 24 | $6.47 \times 10^{-10}$ |
| The compound of Ex. 26 | $7.46 \times 10^{-8}$ |
| The compound of Ex. 27 | $2.18 \times 10^{-6}$ |
| The compound of Ex. 28 | $8.26 \times 10^{-10}$ |

What is claimed is:

1. A carbostyril compound of the formula (1):

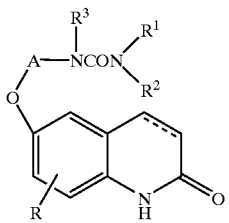

(1)

wherein A is a lower alkylene group,

R is a hydrogen atom, $R^1$ is a cycloalkyl group having a substituent selected from the group consisting of a hydroxy group, a hydroxy-substituted lower alkoxy group, and a lower alkanoyloxy group, $R^2$ is a cycloalkyl group having a substituent selected from the group consisting of a hydroxy group, a hydroxy-substituted lower alkoxy group, and a lower alkanoyloxy group, $R^3$ is a hydrogen atom, and the bond between the 3- and 4-positions of the carbostyril nucleus is a single bond or a double bond, or a salt thereof.

2. A carbostyril compound of the formula (1):

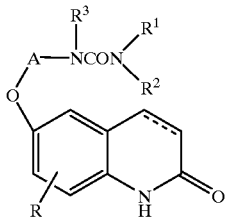

(1)

wherein A is a lower alkylene group,

R is a halogen atom or a lower alkoxy group, $R^1$ and $R^2$ are the same or different and are each a lower alkyl group having optionally a substituent selected from the group consisting of a hydroxy group, a lower alkoxy group, a phenyl-lower alkoxy group, and a lower alkanoyloxy group; a cycloalkyl group having optionally a substituent selected from the group consisting of a hydroxy group, a hydroxy-substituted lower alkoxy group, and a lower alkanoyloxy group; or an amino group having optionally a substituent selected from the group consisting of a lower alkyl group and a cycloalkyl group, $R^3$ is a hydrogen atom, a lower alkyl group, a lower alkenyl group or a hydroxy-substituted lower alkyl group, and the bond between the 3- and 4-positions of the carbostyril nucleus is a single bond or a double bond, or a salt thereof.

3. A carbostyril compound of the formula (1):

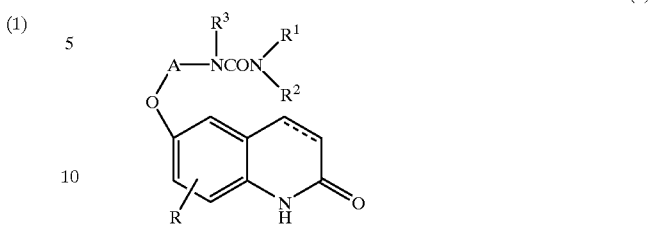

(1)

wherein A is a lower alkylene group,

R is a hydrogen atom, $R^1$ is a cycloalkyl group having optionally a substituent selected from the group consisting of a hydroxy group, a hydroxy-substituted lower alkoxy group, and a lower alkanoyloxy group, $R^2$ is an amino group having optionally a substituent selected from a lower alkyl group and a cycloalkyl group, $R^3$ is a lower alkyl group, a lower alkenyl group or a hydroxy-substituted lower alkyl group, and the bond between the 3- and 4-positions of the carbostyril nucleus is a single bond or a double bond, or a salt thereof.

4. The carbostyril derivative according to claim 2, wherein R is a halogen atom or a lower alkoxy group, and $R^3$ is a hydrogen atom, or a salt thereof.

5. The carbostyril derivative according to claim 2, wherein R is a halogen atom or a lower alkoxy group, and $R^3$ is a lower alkyl group, a lower alkenyl group or a hydroxy-substituted lower alkyl group, or a salt thereof.

6. The carbostyril derivative according to claim 4, wherein $R^1$ and $R^2$ are the same and are each a lower alkyl group having optionally a substituent selected from a hydroxy group, a lower alkoxy group, a phenyl-lower alkoxy group and a lower alkanoyloxy group; a cycloalkyl group having optionally a substituent selected from a hydroxy group, a hydroxy-substituted lower alkoxy group and a lower alkanoyloxy group; or an amino group having optionally a substituent selected from a lower alkyl group and a cycloalkyl group, or a salt thereof.

7. The carbostyril derivative according to claim 4, wherein $R^1$ is a lower alkyl group having optionally a substituent selected from a hydroxy group, a lower alkoxy group, a phenyl-lower alkoxy group and a lower alkanoyloxy group, and $R^2$ is a cycloalkyl group having optionally a substituent selected from a hydroxy group, a hydroxy-substituted lower alkoxy group and a lower alkanoyloxy group; or an amino group having optionally a substituent selected from a lower alkyl group and a cycloalkyl group, or a salt thereof.

8. The carbostyril derivative according to claim 4, wherein $R^1$ is a cycloalkyl group having optionally a substituent selected from a hydroxy group, a hydroxy-substituted lower alkoxy group and a lower alkanoyloxy group, and $R^2$ is an amino group having optionally a substituent selected from a lower alkyl group and a cycloalkyl group, or a salt thereof.

9. The carbostyril derivative according to claim 5, wherein $R^1$ and $R^2$ are the same and are each a lower alkyl group having optionally a substituent selected from a hydroxy group, a lower alkoxy group, a phenyl-lower alkoxy group and a lower alkanoyloxy group; a cycloalkyl group having optionally a substituent selected from a hydroxy group, a hydroxy-substituted lower alkoxy group and a lower alkanoyloxy group; or an amino group having optionally a substituent selected from a lower alkyl group and a cycloalkyl group, or a salt thereof.

10. The carbostyril derivative according to claim 5, wherein $R^1$ is a lower alkyl group having optionally a substituent selected from a hydroxy group, a lower alkoxy group, a phenyl-lower alkoxy group and a lower alkanoyloxy group, and $R^2$ is a cycloalkyl group having optionally a substituent selected from a hydroxy group, a hydroxy-substituted lower alkoxy group and a lower alkanoyloxy group; or an amino group having optionally a substituent selected from a lower alkyl group and a cycloalkyl group, or a salt thereof.

11. The carbostyril derivative according to claim 5, wherein $R^1$ is a cycloalkyl group having optionally a substituent selected from a hydroxy group, a hydroxy-substituted lower alkoxy group and a lower alkanoyloxy group, and $R^2$ is an amino group having optionally a substituent selected from a lower alkyl group and a cycloalkyl group, or a salt thereof.

12. The carbostyril derivative according claims 4 or 5, wherein $R^1$ and $R^2$ are a $C_{3-8}$ cycloalkyl group, which may have a substituent selected from a hydroxy group, a hydroxy-substituted $C_{1-6}$ alkoxy group and a $C_{2-6}$ alkanoyloxy group, or a salt thereof.

13. The carbostyril derivative according to any one of claims 1, 3 or 6–11, wherein the bond between 3- and 4-positions of the carbostyril nucleus is a single bond, or a salt thereof.

14. The carbostyril derivative according to any one of claims 1, 3 or 6–11, wherein the bond between 3- and 4-positions of the carbostyril nucleus is a double bond, or a salt thereof.

15. 6-{3-[3-(trans-2-Hydroxycyclohexyl)-3-cyclopropylureido]-propoxy}carbostyril.

16. (S,S)-(+)-6-{3-[3-(2-Hydroxycyclohexyl)-3-cyclopropylureido]-propoxy}carbostyril.

17. (R,R)-(−)-6-{3-[3-(2-Hydroxycyclohexyl)-3-cyclopropylureido]-propoxy}carbostyril.

18. 6-{3-[3-(2-Hydroxycyclobutyl)-3-cyclopropylureido]propoxy}-carbostyril.

19. 6-{3-[3-(N-Methyl-N-cyclohexylamino)ureido]propoxy}-carbostyril.

20. 6-{3-[3-(N-Cyclopropyl-N-cyclohexylamino)ureido]-propoxy}carbostyril.

21. A pharmaceutical composition comprising, as an active ingredient, a therapeutically effective amount of the compound according to claim 1, or a salt thereof, in admixture with a conventional pharmaceutically acceptable carrier or diluent.

22. A pharmaceutical composition comprising, as an active ingredient, a therapeutically effective amount of the compound according to claim 2, or a salt thereof, in admixture with a pharmaceutically acceptable carrier or diluent.

23. A pharmaceutical composition comprising, as an active ingredient, a therapeutically effective amount of the compound according to claim 3, or a salt thereof, in admixture with a pharmaceutically acceptable carrier or diluent.

24. A method for treating ischemic diseases which comprises administering to a patient in need thereof a therapeutically effective amount of the pharmaceutical composition according to claim 21.

25. The method according to claim 24 where said treatment is an antithrombotic treatment.

26. The method according to claim 24 where said treatment is inhibition of intima thickening.

27. The method according to claim 24 where said treatment is platelet aggregation inhibition.

28. The method according to claim 24 where said treatment is platelet mass dissociation.

29. The method according to claim 24 where said treatment is an increased brain and peripheral vessel blood flow in the brain.

30. A method for treating ischemic diseases which comprises administering to a patient in need thereof a therapeutically effective amount of the pharmaceutical composition according to claim 22.

31. The method according to claim 30 where said treatment is an antithrombotic treatment.

32. The method according to claim 30 where said treatment is inhibition of intima thickening.

33. The method according to claim 30 where said treatment is platelet aggregation inhibition.

34. The method according to claim 30 where said treatment is platelet mass dissociation.

35. The method according to claim 30 where said treatment is an increased brain and peripheral vessel blood flow in the brain.

36. A method for treating ischemic diseases which comprises administering to a patient in need thereof a therapeutically effective amount of the pharmaceutical composition according to claim 23.

37. The method according to claim 36 where said treatment is an antithrombotic treatment.

38. The method according to claim 36 where said treatment is inhibition of intima thickening.

39. The method according to claim 36 where said treatment is platelet aggregation inhibition.

40. The method according to claim 36 where said treatment is platelet mass dissociation.

41. The method according to claim 36 where said treatment is an increased brain and peripheral vessel blood flow in the brain.

* * * * *

UNITED STATES PATENT AND TRADEMARK OFFICE
CERTIFICATE OF CORRECTION

PATENT NO. : 6,143,763
DATED : Nov. 7, 2000
INVENTOR(S) : Yasuo Koga, et al

It is certified that error appears in the above-identified patent and that said Letters Patent is hereby corrected as shown below:

Please delete: [*] Notice: This patent issued on a continued prosecution application filed under 37 C.F.R. § 1.53(d), and is subject to the twenty year patent term provision of 35 U.S.C. § 154(a)(2).

In Item [86]  under § 371 date, change the date to --May 29, 1997-- under § 102(e) date, change the date to --May 29, 1997--.

Signed and Sealed this

Eighth Day of May, 2001

Attest:

NICHOLAS P. GODICI

Attesting Officer      Acting Director of the United States Patent and Trademark Office